(12) United States Patent
Burri et al.

(10) Patent No.: US 7,030,130 B2
(45) Date of Patent: Apr. 18, 2006

(54) BENZOFURAN DERIVATIVES AND THEIR USE AS ANTIBACTERIAL AGENTS

(75) Inventors: Kaspar Burri, Binningen (CH); Dieter Gillessen, Pratteln (CH); Sorana Greiveldinger-Poenaru, Rheinfelden (CH); Khalid Islam, Reinach (CH)

(73) Assignee: Arpida AG, Munchenstein (CH)

( * ) Notice: Subject to any disclaimer, the term of this patent is extended or adjusted under 35 U.S.C. 154(b) by 0 days.

(21) Appl. No.: 10/333,853

(22) PCT Filed: Jul. 20, 2001

(86) PCT No.: PCT/EP01/08426

§ 371 (c)(1),
(2), (4) Date: Jan. 23, 2003

(87) PCT Pub. No.: WO02/10157

PCT Pub. Date: Feb. 7, 2002

(65) Prior Publication Data

US 2004/0034047 A1    Feb. 19, 2004

(30) Foreign Application Priority Data

Jul. 29, 2000  (EP) .................... PCT/EP00/07357

(51) Int. Cl.
*C07D 405/06* (2006.01)
*A61K 31/505* (2006.01)

(52) U.S. Cl. .................... 514/275; 544/323; 544/324

(58) Field of Classification Search ................ 544/323, 544/324; 514/275
See application file for complete search history.

(56) References Cited

U.S. PATENT DOCUMENTS

| 4,438,267 A | 3/1984 | Daluge et al. ............. 544/309 |
| 5,773,446 A | 6/1998 | Masciadri .................. 514/275 |

FOREIGN PATENT DOCUMENTS

| EP | 0 096 214 | 12/1983 |
| GB | 875562 | 8/1961 |

OTHER PUBLICATIONS

Freezor et al., Molecular Characterization of the Acute Inflammatory Response to Infections with Gram-Negative versus Gram-Positive Bacteria, Infection and Immunity, vol. 71, No. 10, pp. 5803-5813, Oct. 2003.*
Snyder et al., PubMed Abstract (J Med Liban 48(4):208-14), Jul.-Aug. 2000.*

* cited by examiner

*Primary Examiner*—Deepak Rao
(74) *Attorney, Agent, or Firm*—Jones Day

(57) ABSTRACT

The invention relates to novel benzofuran derivatives and their use as active ingredients in the preparation of pharmaceutical compositions. The invention also concerns related aspects including processes for the preparation of the compounds, pharmaceutical compositions containing one or more of those compounds and especially their use as anti-infectives.

16 Claims, No Drawings

BENZOFURAN DERIVATIVES AND THEIR USE AS ANTIBACTERIAL AGENTS

This application is a 371 of PCT/EP01/08426 filed Jul. 20, 2001.

The present invention relates to novel 2,4-diamino-5-(substituted) pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR), which catalyses the reduction of dihydrofolic acid to tetrahydrofolic acid (THFA). This property has been shown to result frequently in useful pharmaceutical properties particularly in the treatment of bacterial infections. Thus, U.K. Patent Specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl) pyrimidine, is specifically disclosed in U.K. Patent No. 875, 562 and is the most active general antibacterial agent amongst the 2,4-diamino-5-benzylpyrimidines known to date. Due to their mode of action, these benzylpyrimidines potentiate the antibacterial activity of the sulphonamides, and Trimethoprim has been used extensively over the last decade in human therapy in combination with various sulphonamides, and in particular with sulphamethoxazole, for the treatment of bacterial infections.

European Patent Applications Nos. 81109631.2 and 83104240.3 disclose inter alia also such type of compounds and their use.

It has now been found that a group of novel benzofuran derivatives is more potent than e.g. Trimethoprim and is especially active against Gram positive pathogens like *Staphylococcus aureus, Staphylococcus epidermidis, Enterococcus faecalis* or *Streptococcus pneumoniae* and at the same time also against Gram negative pathogens like *Haemophilus influenzae, Escherichia coli, Klebsiella pneumoniae* or *Proteus vulgaris*. The compounds proved to be especially potent against respiratory tract pathogens.

Therefore, the present invention relates to novel compounds of the general formula I

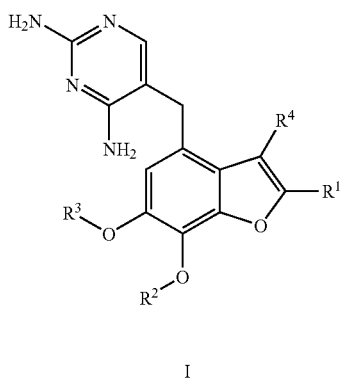

Formula I wherein $R^1$ represents straight or branched chain lower alkyl with 2 to 6 carbon atoms; cycloalkylmethyl with 3 to 6 carbon atoms; aryl; arylmethyl or heteroarymethyl, the aryl and heteroaryl group may be mono-, di- or tri-substituted with halogen, amino, hydroxy, nitro, trifluoromethyl, lower alkyloxy, lower alkylcarbonylamino, arylcarbonylamino, whereby these substituents may be the same or different; straight or branched chain lower alkylcarbonyl with up to 6 carbon atoms; cycloalkylcarbonyl with 3 to 6 carbon atoms; cycloalkylhydroxymethyl with 3 to 6 carbon atoms; arylcarbonyl, the aryl group may be mono-, di or tri-substituted with halogen, amino, lower alkyloxy, lower alkylcarbonylamino, arylcarbonylamino, whereby these substituents may be the same or different; arylhydroxymethyl, the aryl group may be mono-, di- or tri-substituted with halogen, amino, lower alkyloxy, lower alkylcarbonylamino, arylcarbonylamino, whereby these substituents may be the same or different; straight or branched chain lower alkenyl with 2 to 6 carbon atoms; hydroxy-lower alkyl with 1 to 6 carbon atoms; fluoro-lower alkyl with 1 to 6 carbon atoms; aryloxy-lower alkyl whereby the aryl group may be mono-, di- or tri-substituted with halogen, amino, lower alkyloxy, lower alkylcarbonylamino, arylcarbonylamino, whereby these substituents may be the same or different; arylthio-lower alkyl whereby the aryl group may be mono-, di- or tri-substituted with halogen, amino, lower alkyloxy, lower alkylcarbonylamino, arylcarbonylamino, whereby these substituents may be the same or different; arylamino-lower alkyl whereby the aryl group may be mono-, di- or tri-substituted with halogen, amino, lower alkyloxy, lower alkylcarbonylamino, arylcarbonylamino, whereby these substituents may be the same or different; lower alkenyloxy lower alkyl whereby the lower alkenyl group may contain 2 to 4 carbon atoms and the lower alkyl group may contain 1 or 2 carbon atoms; benzyloxy lower alkyl whereby the benzyl group may be mono-, di- or tri-substituted with halogen, amino, lower alkyloxy, lower alkylcarbonylamino, arylcarbonylamino, whereby these substituents may be the same or different; lower alkylamino lower alkyl whereby the lower alkyl groups may contain 1 to 3 carbon atoms; heterocyclylmethyl containing one to three hetero atoms which can be the same or different and which may be substituted with lower alkyl, halogen, amino, lower alkyloxy, hydroxy, lower alkylcarbonylamino, arylcarbonylamino and benzofused derivatives thereof.

$R^2$ and $R^3$ independently represent hydrogen; lower alkyl with 1 to 3 carbon atoms; or together a lower alkylene group with 1 to 3 carbon atoms bridging the oxygen atoms and forming a five, six or seven membered ring;

$R^4$ represents hydrogen; straight or branched chain lower alkyl with 1 to 4 carbon atoms;

and pharmaceutically acceptable salts and N-oxides thereof.

In the definitions of the general formula I—if not otherwise stated—the expression lower means straight and branched chain groups with either one or two to six or three carbon atoms, preferably 1 to 3 carbon atoms. Examples of lower alkyl and lower alkoxy groups are methyl, ethyl, n-propyl, isopropyl, n-butyl, isobutyl, sec.-butyl, tert.-butyl, pentyl, hexyl, trifluoromethyl, chloromethyl, fluoromethyl, hydroxymethyl, carbahdehyd, thiomethyl, methoxy, ethoxy, propoxy, butoxy, iso-butoxy, sec.-butoxy and tert.-butoxy. Lower alkylene groups as bridging two oxygen atoms are preferably methylen(-dioxy), ethylen(-dioxy) and propylen (-dioxy) groups and forming in this way a five-, six- or seven-membered ring. Examples of lower alkanoyl-groups are acetyl, propanoyl and butanoyl. Lower alkenylen means e.g.vinylen, propenylen and butenylen. Lower alkenyl and lower alkynyl means groups like ethylen, propylen, butylen, 2-methyl-propenyl, and ethinylen, propinylen, butinylen, pentinylen, 2-methyl-pentinylen etc. Lower alkenyloxy means allyloxy, vinyloxy, propenyloxy and the like. The expression cycloalkyl means a saturated cyclic hydrocarbon ring with 3 to 6 carbon atoms, e.g. cyclopropyl, cyclobutyl, cyclopentyl and cyclohexyl, which may be substituted with lower alkyl, hydroxy-lower alkyl, amino-lower alkyl, lower alkoxy-lower alkyl and lower alkenylen groups. The expression heteroaryl means six-membered aromatic rings containing one to four nitrogen atoms, benzofused six-membered aromatic rings containing one to three nitrogen atoms, five-membered aromatic rings containing one oxygen or one nitrogen or one sulfur atom, benzo- fused five-membered aromatic rings containing one oxygen or one nitrogen or one sulfur atom, five membered aromatic rings containig an oxygen and nitrogen atom and benzo fused derivatives thereof, five-membered aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring e.g. furanyl, thienyl, pyrrolyl, pyridinyl, indolyl, quinolinyl, isoquinolinyl, imidazolyl, triazinyl, thiazinyl, thiazolyl, isothiazolyl, pyridazinyl, oxazolyl, isoxazolyl, etc. whereby such rings may be substituted with lower alkyl, lower alkenyl, amino, amino-lower alkyl, halogen, hydroxy, lower alkoxy, trifluoromethoxy or trifluoromethyl. The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyl-oxy, lower alkenylen, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkyloxy-lower alkyl, lower alkyloxy-lower alkyloxy, trifluoromethyl, trifluoromethoxy, cycloalkyl, hydroxy-cycloalkyl, heterocyclyl, heteroaryl. The expression heterocyclyl represents saturated and unsaturated, but not aromatic, three- to six-membered rings containing one to three nitrogen, oxygen or sulfur atoms which may be the same or different like azyridinyl, piperidinyl, mopholinyl, piperazinyl, tetrahydropyranyl, dihydropyranyl, 1,4-dioxanyl, pyrrolidinyl, tetrahydrofuranyl, dihydroimidazolyl, dihydropyrazoyl, pyrazolidinyl, tetrahydroquinolinyl, tetrahydroisoquinolinyl, dihydroquinilinyl, dihydroisoquinolinyl.

Preferred compounds are compounds of formula I, wherein $R^1$ is straight or branched chain lower alkyl with 2 to 6 carbon atoms; cycloalkylmethyl with 3 to 6 carbon atoms; aryl; arylmethyl or heteroarymethyl, the aryl and heteroaryl group may be mono- or di substituted with halogen, amino, hydroxy, nitro, trifluoromethyl, lower alkyloxy, lower alkylcarbonylamino, arylcarbonylamino, whereby these substituents may be the same or differen, and $R^2$ and $R^3$ are methyl or together are a methylen group bridging the oxygen atoms to which they are attached and $R^4$ is hydrogen or methyl.

Especially preferred compounds are compounds of formula I, wherein $R^1$ is 4-methoxy-benzyl, phenyl, benzyl, cyclopropylmethyl, 4-fluoro-benzyl, 3,4-dihydro-1H-isoquinolin-2-ylmethyl, 4-methoxy-benzyloxymethyl, 4-acetylaminophenyl-sulfanyl-methyl, 4-trifluoromethyl-phenoxymethyl, 4-amino-phenoxymethyl, allyloxymethyl, phenyl-[1,3]dioxolan-2-yl, pyrrol-1-ylmethyl, 3,4-dimethoxy-benzyl, 4-hydroxyphenyloxymethyl, phenylcarbonylmethyl, 4-fluoro-phenoxymethyl, 2,2-dimethyl-propyl, 4-fluoro-phenylsulfanylmethyl, hydroxymethyl, formyl, 4-fluoro-phenylamino-methyl, imidazol-1-ylmethyl, dimethylaminomethyl, morpholin-4-ylmethyl, biphenyl-4-ylmethyl, ethoxycarbonyl, carboxy, 4-hydroxybenzyl, furan-2-ylmethyl, thiophen-2-ylmethyl, thiophen-3-ylmethyl, 1-methyl-pyrrol-2-ylmethyl, pyridin-2-ylmethyl, pyridin-3-ylmethyl, pyridin-4-ylmethyl, 4-acetylaminobenzyl, 4-amino-benzyl, 4-nitro-benzyl, 4-acetylamino-3-methoxy-benzyl, 4-amino-3-methoxy-benzyl, 3-acetylamino-4-methoxy-benzyl, 3-amino-4-methoxy-benzyl, allyl, isopropenyl or halogenmethyl, and $R^2$ and $R^3$ are methyl or together are a methylen group bridging the oxygen atoms to which they are attached and $R^4$ is hydrogen or methyl.

Very preferred compounds are compounds of formula I, wherein $R^1$ is 4-methoxy-benzyl, phenyl, benzyl, cyclopropylmethyl, 4-fluoro-benzyl, 3,4-dihydro-1H-isoquinolin-2-ylmethyl, 4-methoxy-benzyloxymethyl, 4-acetylaminophenyl-sulfanyl-methyl, 4-trifluoromethyl-phenoxymethyl, 4-amino-phenoxymethyl, allyloxymethyl, 3,4-dimethoxybenzyl, 4-hydroxybenzyl, pyridin-2-ylmethyl, pyridin-3-ylmethyl, pyridin-4-ylmethyl, 4-acetylaminobenzyl, 4-aminobenzyl, 4-acetylamino-3-methoxy-benzyl, 4-amino-3-methoxy-benzyl, 3-acetylamino-4-methoxy-benzyl, 3-amino-4-methoxy-benzyl or aryl methyl and $R^2$ and $R^3$ are both methyl and $R^4$ is hydrogen.

Most preferred compounds are compounds of formula I, wherein $R^1$ is 4-methoxy-benzyl, benzyl, cyclopropylmethyl, 4-fluoro-benzyl, 3,4-dihydro-1H-isoquinolin-2-ylmethyl, 4-amino-phenoxymethyl, 4-hydroxybenzyl, pyridin-2-ylmethyl, pyridin-3-ylmethyl, pyridin-4-ylmethyl, 4-acetylaminobenzyl, 4-amino-benzyl, 4-acetylamino-3-methoxy-benzyl, 4-amino-3-methoxy-benzyl, 3-acetylamino-4-methoxy-benzyl, 3-amino-4-methoxy-benzyl and $R^2$ and $R^3$ are both methyl and $R^4$ is hydrogen Preferred compounds of the present invention include:
 5-[6,7-Dimethoxy-2-(4-methoxy-benzy)benzofuran-4-ylmethyl]pyrimidine-2,4-diamine,
 5-(6,7-Dimethoxy-2-phenyl-benzofuran-4-ylmethyl)-pyrimidine-2,4-diamine,
 5-(2-Benzyl-6,7-dimethoxy-benzofuran-4-ylmethyl)-pyrimidine-2,4-diamine,
 5-(2-Cyclopropylmethyl-6,7-dimethoxy-benzofuran-4-ylmethyl)-pyrimidine-2,4-diamine,
 5-[2-(4-Fluoro-benzyl)-6,7-dimethoxy-benzofuran-4-ylmethyl]-pyrimidine-2,4-diamine,
 5-[2-(3,4-Dihydro-1H-isoquinolin-2-ylmethyl)-6,7-dimethoxy-benzofuran-4-ylmethyl]-pyrimidine-2,4-diamine,
 5-[6,7-Dimethoxy-2-(4-methoxy-benzyloxymethyl)-benzofuran-4-ylmethyl]-pyrimidine-2,4-diamine,
 N-{4-[4-(2,4-Diamino-pyrimidin-5-ylmethyl)-6,7-dimethoxy-benzofuran-2-ylmethylsulfanyl]-phenyl}-acetamide,
 5-[6,7-Dimethoxy-2-(4-trifluoromethyl-phenoxymethyl)-benzofuran-4-ylmethyl]-pyrimidine-2,4-diamine,
 5-[2-(4-Amino-phenoxymethyl)-6,7-dimethoxy-benzofuran-4-ylmethyl]-pyrimidine-2,4-diamine,
 5-(2-Allyloxymethyl-6,7-dimethoxy-benzofuran-4-ylmethyl)-pyrimidine-2,4-diamine,
 5-[6,7-Dimethoxy-2-(2-phenyl-[1,3]dioxolan-2-yl)-benzofuran-4-ylmethyl]-pyrimidine-2,4-diamine,
 5-(6,7-Dimethoxy-2-pyrrol-1-ylmethyl-benzofuran-4-ylmethyl)-pyrimidine-2,4-diamine, 5-[2-(3,4-Dimethoxy-benzyl)-6,7-dimethoxy-benzofuran-4-ylmethyl]-pyrimidine-2,4-diamine,
4-[4-(2,4-Diamino-pyrimidin-5-ylmethyl)-6,7-dimethoxy-benzofuran-2-ylmethoxy]-phenol,
[4-(2,4-Diamino-pyrimidin-5-ylmethyl)-6,7-dimethoxy-benzofuran-2-yl]-phenyl-methanone,
5-[2-(4-Fluoro-phenoxymethyl)-6,7-dimethoxy-benzofuran-4-ylmethyl]-pyrimidine-2,4-diamine,
5-[2-(2,2-Dimethyl-propyl)-6,7-dimethoxy-benzofuran-4-ylmethyl]pyrimidine-2,4-diamine,
5-[2-(4-Fluoro-phenylsulfanylmethyl)-6,7-dimethoxy-benzofuran-4-ylmethyl]-pyrimidine-2,4-diamine,
[4-(2,4-Diamino-pyrimidin-5-ylmethyl)-6,7-dimethoxy-benzofuran-2-y-]-methanol,
4-(2,4-Diamino-pyrimidin-5-ylmethyl)-6,7-dimethoxy-benzofuran-2-carbaldehyde
5-{2-[(4-Fluoro-phenylamino)-methyl]-6,7-dimethoxy-benzofuran-4-ylmethyl}-pyrimidine-2,4-diamine,
5-(2-Imidazol-1-ylmethyl-6,7-dimethoxy-benzofuran-4-ylmethyl)-pyrimidine-2,4-diamine,
5-(2-Dimethylaminomethyl-6,7-dimethoxy-benzoturan-4-ylmethyl)-pyrimidine-2,4-diamine,
5-(6,7-Dimethoxy-2-morpholin-4-ylmethyl-benzofuran-4-ylmethyl)-pyrimidine-2,4-diamine,
5-(2-Biphenyl-4-ylmethyl-6,7-dimethoxy-benzofuran-4-ylmethyl)-pyrimidine-2,4-diamine,
4-(2,4-Diamino-pyrimidin-5-ylmethyl)-6,7-dimethoxy-3-methyl-benzofuran-2-carboxylic acid,
4-(2,4-Diamino-pyrimidin-5-ylmethyl)-6,7-dimethoxy-3-methyl-benzofuran-2-carboxylic acid ethyl ester,
5-[6,7-Dimethoxy-2-((4-chlorobenzyl)-benzofuran-4-ylmethyl]pyrimidine-2,4-diamine,
5-[6,7-Dimethoxy-2-(1-naphthylmethyl)-benzofuran-4-ylmethyl]pyrimidine-2,4-diamine,
5-[6,7-Dimethoxy-2-(2-propenyl)benzofuran-4-ylmethyl]pyrimidine-2,4-diamine,
5-(6,7-Dimethoxy-2-trifluoromethylbenzofuran-4-ylmethyl )pyrimidine-2,4-diamine,
5-[6,7-Dimethoxy-2-(2,2-dimethylpropan1-one)benzofuran-4-ylmethyl]pyrimidine-2,4-diamine,
5-[6,7-Dimethoxy-2-(cyclopropylcarbonyl)benzofuran-4-ylmethyl]pyrmidine-2,4-diamine,
5-[6,7-Dimethoxy-2-(4-methoxyphenyl-methanone)benzofuran-4-ylmethyl]pyrimidine-2,4-diamine,
5-[6,7-Dimethoxy-2-(4-chlorophenyl-methanone 1)benzofuran-4-ylmethyl]pyrimidine-2,4-diamine,
5-[6,7-Dimethoxy-2-(4-fluorophenyl-methanone)benzofuran-4-ylmethyl]pyrimidine-2,4-diamine,
5-[6,7-Dimethoxy-2-(1-naphthyl methanone)-benzofuran-4-ylmethyl]pyrimidine-2,4-diamine,
5-[6,7-Dimethoxy-2-(2,2-dimethyl-1-hydroxypropyl)-benzofuran-4-ylmethyl]pyrimidine-2,4-diamine,
5-[6,7-Dimethoxy-2-(cyclopropylmethanol)-benzofuran-4-ylmethyl]pyrimidine-2,4-diamine,
5-[6,7-Dimethoxy-2-(phenylmethanol)benzofuran-4-ylmethyl]pyrimidine-2,4-diamine,
5-[6,7-Dimethoxy-2-((4-methoxyphenylmethanol)-benzofuran-4-ylmethyl]pyrimidine-2,4-diamine,
5-[6,7-Dimethoxy-2-((4-chlorophenyl)methanol)-benzofuran-4-ylmethyl]pyrimidine-2,4-diamine,
5-[6,7-Dimethoxy-2-((4-fluorophenylmethanol)-benzofuran-4-ylmethyl]pyrimidine-2,4-diamine,
5-[6,7-Dimethoxy-2-(1-naphthylmethanol)-benzofuran-4-ylmethyl]pyrimidine-2,4-diamine,
5-[2-(3,4-Dihydro-2H-quinolin-1-ylmethyl)-6,7-dimethoxy-benzofuran-4-ylmethyl]-pyrimidine-2,4-diamine,
5-[6,7-Dimethoxy-2-(tetrazol-5-ylmethyl)benzofuran-4-ylmethyl]pyrimidine-2,4-diamine,
5-[6,7-Dimethoxy-2-(indol-1-ylmethyl)benzofuran-4-ylmethyl]pyrimidine-2,4-diamine,
5-[6,7-Dimethoxy-2-(imidazol-1-ylcarbonyl)benzofuran-4-ylmethyl]pyrimidine-2,4-diamine,
5-(2-Furan-2-ylmethyl-6,7-dimethoxy-benzofuran-4-ylmethyl)-pyrimidine-2,4-diamine,
5-(6,7-Dimethoxy-2-thiophen-2-ylmethyl-benzofuran-4-ylmethyl)-pyrimidine-2,4-diamine,
5-[6,7-Dimethoxy-2-(1-methyl-1H-pyrrol-2-ylmethyl)-benzofuran-4-ylmethyl]-pyrimidine-2,4-diamine,
5-(6,7-Dimethoxy-2-pyridin-2-ylmethyl-benzofuran-4-ylmethyl)-pyrimidine-2,4-diamine,
5-(6,7-Dimethoxy-2-pyridin-3-ylmethyl-benzofuran-4-ylmethyl)-pyrimidine-2,4-diamine,
5-(6,7-Dimethoxy-2-pyridin-4-ylmethyl-benzoturan-4-ylmethyl)-pyrimidine-2,4-diamine,
4-[4-(2,4-Diamino-pyrimidin-5-ylmethyl)-6,7-dimethoxy-benzofuran-2-ylmethyl]-phenol,
N-{4-[4-(2,4-Diamino-pyrimidin-5-ylmethyl)-6,7-dimethoxy-benzofuran-2-ylmethyl]-phenyl}-acetamide,
5-[2-(4-Amino-benzyl)-6,7-dimethoxy-benzofuran-4-ylmethyl]-pyrimidine-2,4-diamine,
5-[6,7-Dimethoxy-2-(4-nitro-benzyl)-benzofuran-4-ylmethyl]-pyrimidine-2,4-diamine,
N-{4-[4-(2,4-Diamino-pyrimidin-5-ylmethyl)-6,7-dimethoxy-benzofuran-2-ylmethyl]-2-methoxy-phenyl}-acetamide,
5-[2-(4-Amino-3-methoxy-benzyl)-6,7-dimethoxy-benzofuran-4-ylmethyl]-pyrimidine-2,4-diamine,
N-{5-[4-(2,4-Diamino-pyrimidin-5-ylmethyl)-6,7-dimethoxy-benzofuran-2-ylmethyl]-2-methoxy-phenyl}-acetamide,
5-[2-(3-Amino-4-methoxy-benzyl)-6,7-dimethoxy-benzofuran-4-ylmethyl]-pyrimidine-2,4-diamine,
5-(6,7-Dimethoxy-2-thiophen-3-ylmethyl-benzofauran-4-ylmethyl)-pyrimidine-2,4-diamine, and pharmaceutically acceptable salts and N-oxides thereof.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methanesulfonic acid, p-toluenesulfonic acid and the like or in case the compound of formula I is acidic in nature with an inorganic base like an alkali or earth alkali base, e.g. sodium hydroxide, potassium hydroxide, calcium hydroxide etc.

Because of their ability to inhibit Gram positive and Gram negative bacteria, the described compounds can be used for the treatment of diseases which are associated with an infection by such type of pathogens. They are valuable anti-infectives.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intra-muscular, or oral administrations as well as eye drops. The dosage used depends upon the type of the specific active ingredient, the age and the requirements of the patient and the kind of application. Generally, dosages of 0.1–50 mg/kg body weight per day are considered. The preparations with compounds of formula I can contain inert or as well pharmacodynamically active excipients like sulphonamides. Tablets or granules, for example, could contain a number of binding agents, filling excipients, carrier substances or diluents.

These compositions may be administered in enteral or oral form e.g. as tablets, dragees, gelatine capsules, emulsions, solutions or suspensions, in nasal form like sprays or rectally in form of suppositories. These compounds may also be administered in intramuscular, parenteral or intraveneous form, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, antioxidants etc.

The compounds of formula I may also be used in co-therapy with one or more other therapeutically used classes of antimicrobial substances, for example, β-lactams e.g. penicillins and cephalosporins; glycopeptides; quinolones; tetracyclines; aminoglycosides; macrolides etc.

The dosage may vary within wide limits but should be adapted to the specific situation. In general the dosage given in oral form should daily be between about 3 mg and about 4 g, preferably between about 0.2 g and about 4 g, especially preferred between 0.2 g and 2 g per adult with a body weight of about 70 kg. The dosage should be administered preferably in 1 to 3 doses per day which are of equal weight. As usual children should receive lower doses which are adapted to body weight and age.

The invention also relates to a process for the manufacture of compounds of formula I

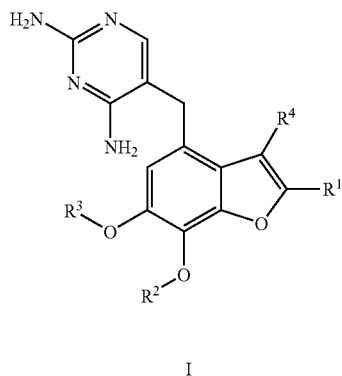

Formula I wherein
$R^1$, $R^2$, $R^3$ and $R^4$ have the meaning given in formula I above,
which process comprises reacting—as depicted in Scheme 1—a compound of the general formula III (obtained from a gallate derivative II: either by Friedel-Crafts acylation, or via a Vilsmeyer aldehyde synthesis (K. Hayashi, K. Tokura, K. Okabe, K. Yamamoto, and K Tawara, *Chem. Pharm. Bull.* 1982, 30, 2860–2869), or by formylation with dichloromethoxymethane, see experimental part), with boron trichloride or boron tribromide at temperatures between −70° C. and 0° C. The methoxy group adjacent to the acyl group is thereby selectively cleaved, to yield ortho-acyl phenol derivatives of the general formula IV:

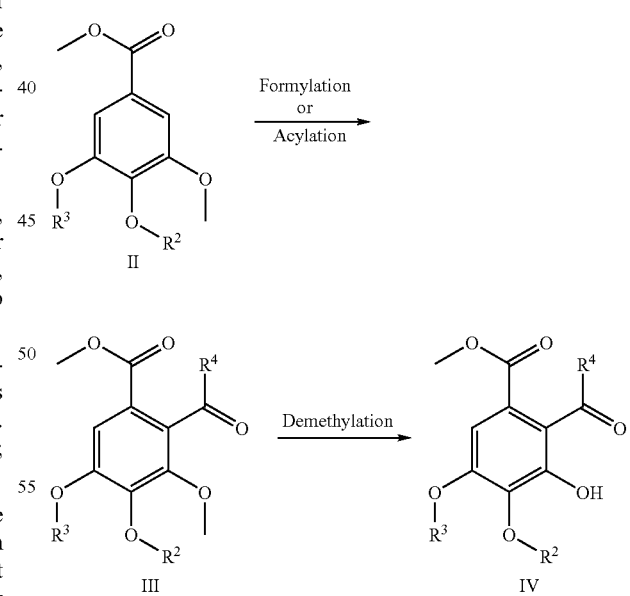

Subsequently, the compounds IV, wherein $R^2$, $R^3$, and $R^4$ have the meaning given in formula I above, are reacted with α-bromomethyl ketones $R^5$—CO—CH$_2$Br V in the presence of potassium carbonate, to yield 2-acylated benzofuran derivatives VI (Scheme 2)
whereby in formula V $R^5$ represents straight or branched chain lower alkyl with 1 to 5 carbon atoms; cycloalkyl with 3 to 6 carbon atoms; aryl or heteroaryl, the aryl and heteroaryl group may be mono-, di- or tri-substituted with halogen, amino, lower alkyloxy, lower alkylcarbonylamino, arylcarbonylamino, whereby these substituents may be the same or different; straight or branched chain lower alkenyl with 2 to 6 carbon atoms.

The carbonyl group of VI can then be removed selectively by reducing it with sodium cyanoborohydride in the presence of trimethylsilyl chloride, to yield the benzofuran ester derivatives IX, wherein $R^1$, $R^2$, $R^3$, and $R^4$ have the meaning given in formula I.

Scheme 3

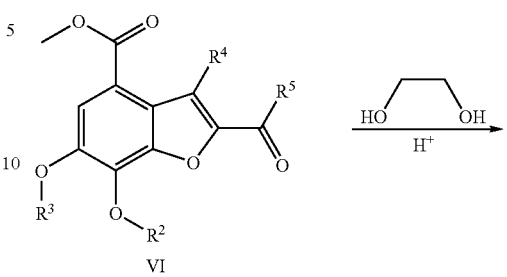

Scheme 2

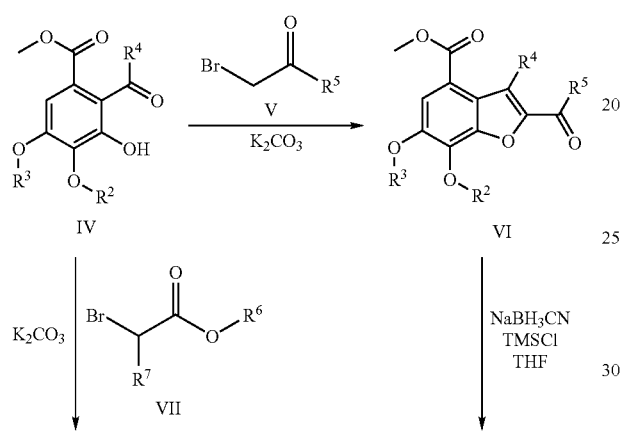

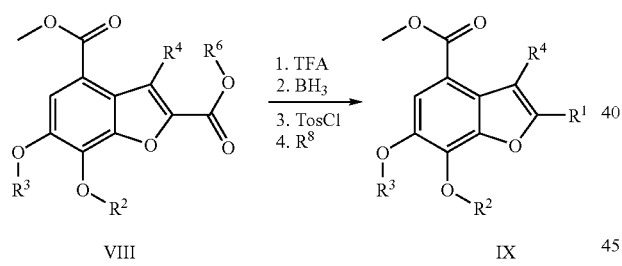

Alternatively, benzofurans of the general structure IX can be obtained by reacting IV with an (α-bromo-ester derivative $R^6OCO$—$CH(Br)$—$R^7$ VII ($R^6$ is tert-butyl, and $R^7$ may be hydrogen or tert-butoxycarbonyl), again in the presence of carbonate, to give benzofuran dicarboxylates of the formula VIII, whereby $R^2$, $R^3$, and $R^4$ have the meaning given in formula I, and $R^6$ represents the tert-butyl group. The latter can be cleaved selectively with trifluoroacetic acid, and may then be reduced preferentially with diborane. The resulting primary alcohol is then converted into a leaving group, e.g. a tosylate, which is then displaced by a nucleophile $R^8$, such as a nitrogen-containing heteroaromatic moiety to yield IX wherein $R^1$ equals $R^8CH_2$—.

If the acyl group in formula VI (Scheme 2) is to be preserved, i.e. if in the final product (formula I) $R^1$ represents an acyl group (cycloalkylcarbonyl, arylcarbonyl etc.), it may be protected as an ethylene ketal, as set forth in structure X (Scheme 3):

In a third alternative approach described in Scheme 4, phenol XI (Wipf, P.; Weiner, W. S. *J. Org. Chem.* 1999, 64, 5321–5324) is reacted with a propargylic alcohol derivative XII under Mitsunobu conditions (diethyl azodicarboxylate and triphenyl phosphine) to afford the phenyl ethers XIII. After cleaving off the trimethylsilyl protecting group with potassium carbonate, the resulting free acetylenes can be rearranged, as described previously (Koch-Pomeranz, U.; Hansen, H.-J.; Schmid, H. *Helv. Chim. Acta* 1973, 56, 2981–3004), to benzofurans IX.

Scheme 4

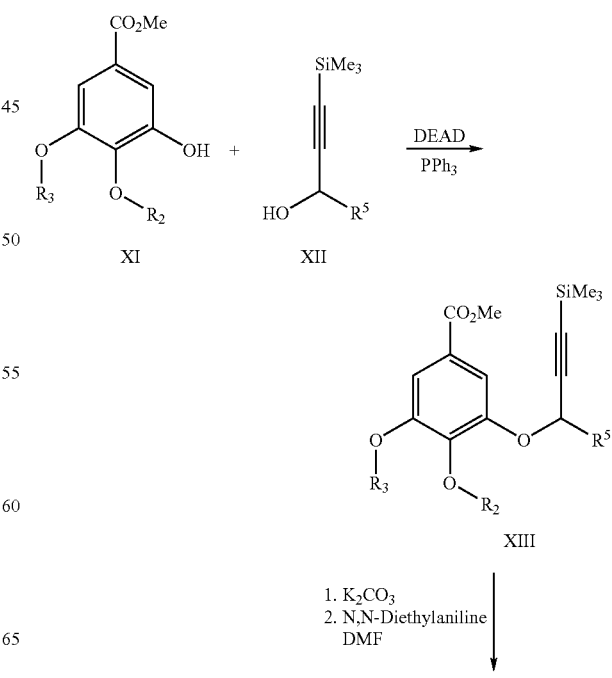

-continued

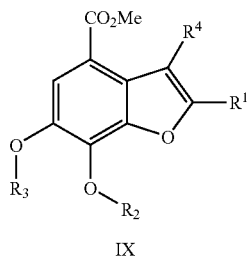

IX

Scheme 5

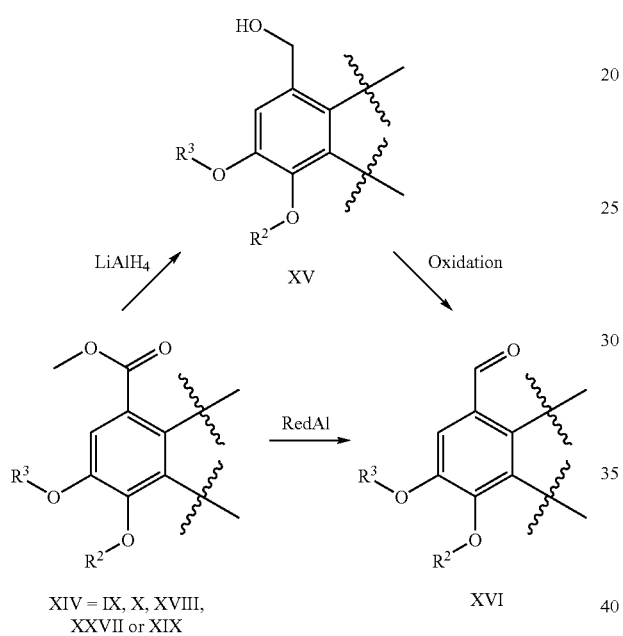

The manufacturing process then continues as depicted in Scheme 5. The ester function of the general substructure XIV (consisting of either IX or X) is reduced to an aldehyde XVI, either directly, with an organoaluminum hydride reagent, or in two steps, via the primary alcohol XV.

Finally, the aldehyde group is transformed into the diaminopyrimidine ring, employing the standard technology outlined in Scheme 6.

Scheme 6

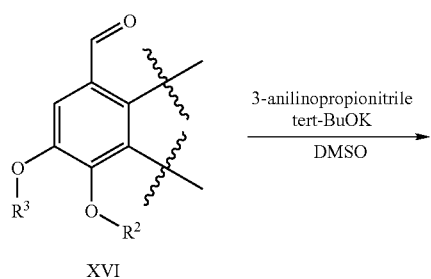

-continued

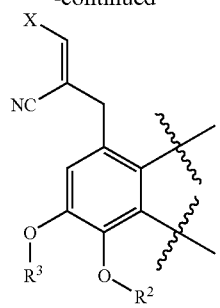

XVII

Thus, compounds of formula I can be obtained; if $R^1$ represents an acyl group, i.e. structure XVII has been the intermediate, the final elaboration includes an acid-induced removal of the ketal protecting group.

Scheme 7

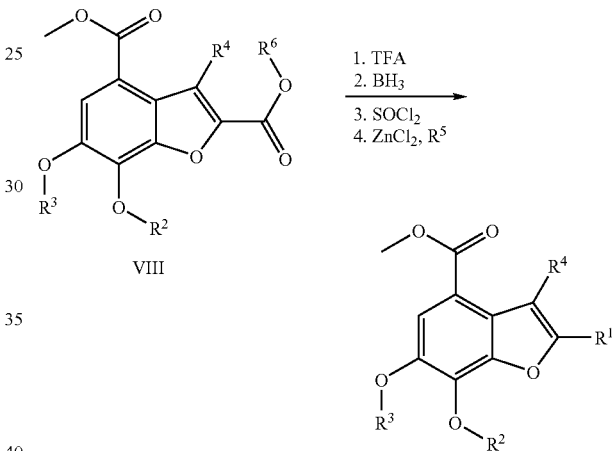

Access to an alternative array of substituents can be gained by proceeding according to Scheme 7: The diester VII (Schemes 2 and 7), if $R^6$ represents a tert.-butyl group, can be cleaved selectively with trifluoroacetic acid, yielding VIII, $R^6$=H. This carboxylic acid may then be reduced with diborane to the primary alcohol IX, $R^1$=CH$_2$OH.

Treatment with thionyl chloride affords IX, $R^1$=CH$_2$Cl. This very active halide can now be employed as one component in the Lewis acid (preferably ZnCl$_2$) catalysed Friedel-Craft's alkylation, the $R^5$ component being either an electron-rich aryl or heteroaryl group which may be mono-, di- or tri-substituted with halogen, amino, lower alkyloxy, lower alkylcarbonylamino, arylcarbonylamino, such as phenol, 1,2-dimethoxybenzene, 2-methoxyphenacetin, furan, thiophene, 1-methylpyrrol. The product is compound IX, wherein $R^1$, $R^2$, $R^3$, and $R^4$ have the meaning given in formula I Yet another alternative to 2-substituted benzofurans is described in Scheme 8:

Here the same ester VII, $R^6$=tert.-butyl, is cleaved with trifluoroacetic acid, and the resulting carboxylic acid VII, $R^6$=H can be coupled in peptide fashion with primary or secondary amines $R^8$, producing the carboxamides XVIII, wherein $R_8$ may be a mono- or di-lower alkylamino group, aminoaryl or heterocycle acylated at the secondary amine group, such as morpholin-4-yl or tetrahydroisoquinoline-2-yl and $R^2$, $R^3$, and $R^4$ have the meaning given in formula I.

Scheme 8

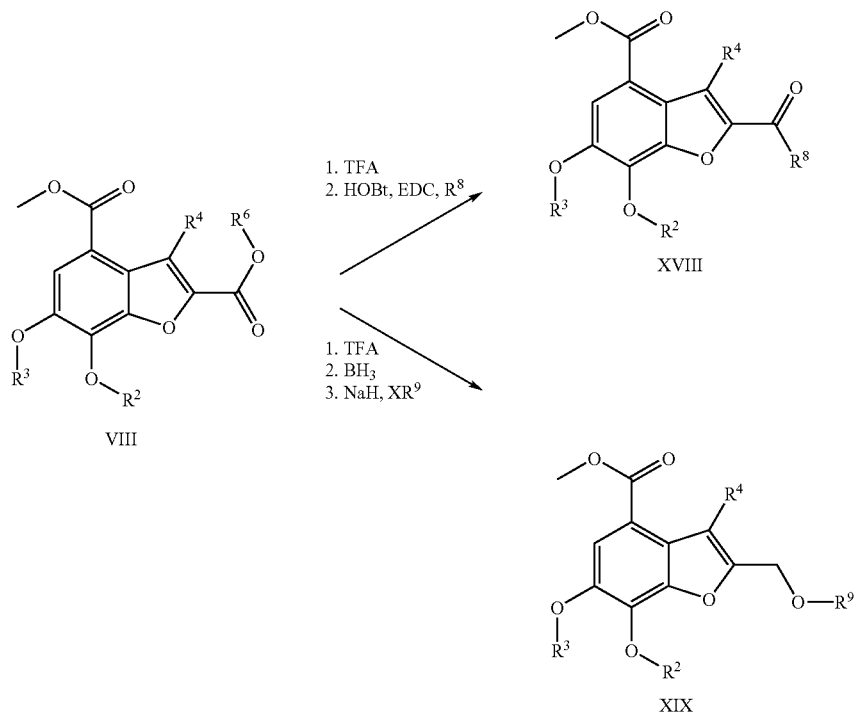

A different pattern of substituents results, when the free acid VIII, $R^6$=H is reduced, as in Scheme 7, to the primary alcohol XIX, $R^9$=H (this compound is identical with IX, $R^1$=CH$_2$OH of Scheme 7). This alcohol in turn may be transformed into ether derivatives XIX by alkylating its sodium salt with very reactive halides such as allyl bromide or benzyl bromide, wherein $R^9$ may be lower alkyl, lower alkenyl, or arylmethyl and $R^2$, $R^3$, and $R^4$ have the meaning given in formula I The final elaboration of the intermediates IX, XVIII and XIX of the Schemes 7 and 8 into diaminopyrimidines is then carried out in analogy to the Schemes 5 and 6.

If so desired, the operations summarised in the Schemes 7 and 8 may be carried out in a more convergent fashion closer to the end of the synthesis:

Scheme 9

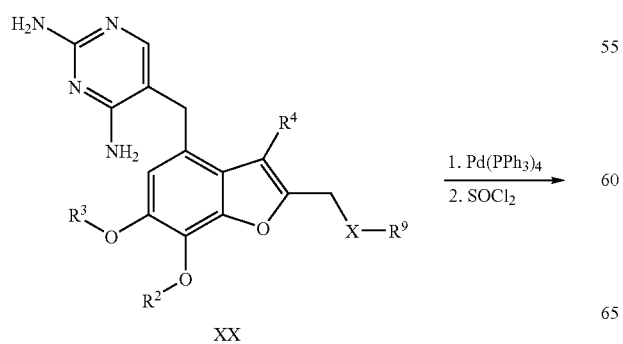

-continued

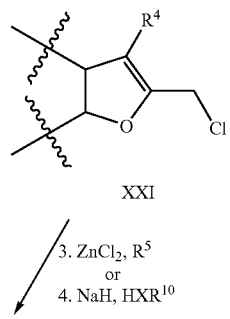

Thus, as in Scheme 9, from the allyl protected product XX (obtained from XIX, $R^9$=allyl, in Scheme 8 by construction of the pyrimidine ring according to Schemes 5 and 6) the hydroxymethl group can be liberated by isomerising of the allyl group with Pd(PPh$_3$)$_4$ and then hydrolizing the resulting enol ether. Treatment with thionyl chloride affords the reactive chloride XXI, which, in turn can be employed as a Friedel-Craft's component as described in Scheme 7, or which can be used to O—N— or S-alkylate with $HXR^{10}$, wherein X may be one oxygen or one nitrogen or one sulfur and R10 alkyl or aryl groups such as phenols, primary or secondary alkyl- or dialkylamines and aryl(alkyl)amines, thiophenols, pyrrol, indol, imidazol or tetrazol to yield compounds of formula I.

An even more convergent approach to is outlined in Scheme 10:

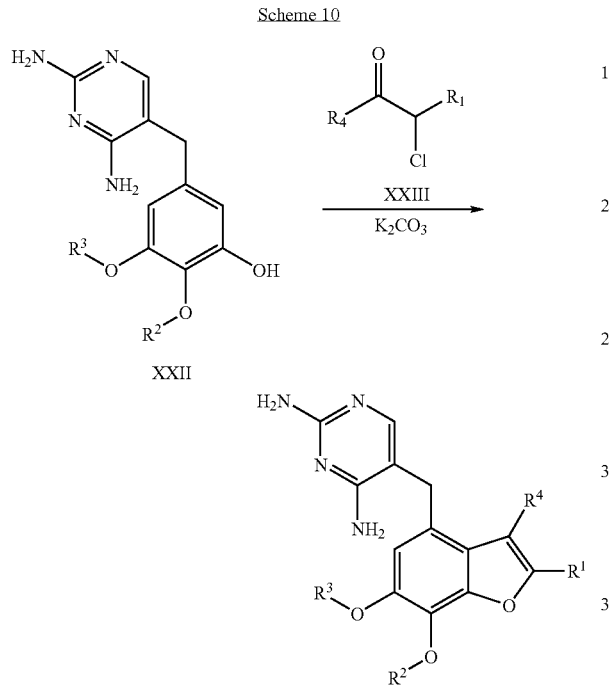

Here, the demethylated phenol XXII (G. Rey-Bellet and R. Reiner Helv. Chim. Acta 1970, 53, 945) is treated with α-chlorinated aldehydes (or ketones) XXIII wherein $R^1$ and $R^4$ have the meaning given in formula I, in the presence of potassium carbonate, yielding the final products I directly.

Another convergent approach (Scheme 11) consists in brominating the phenol XXIV and coupling the resulting bromophenol XXV with acetylenic component XXVI as described in the literature (J. Org. Chem. 1996, 61, 9280–9288; Bioorg. Med. Chem. 1999, 7, 6, 1131–1140).

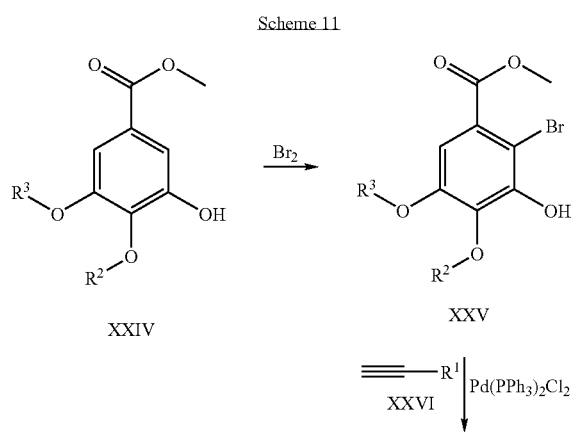

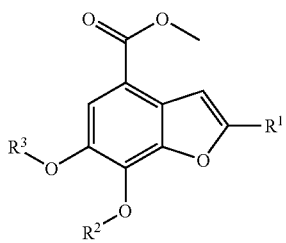

The coupled acetylene then closes spontaneously to the corresponding benzofuran XXVII.

EXAMPLES

Abbreviations:
ACN: Acetonitrile
ATCC: American type culture collection
DEAD: Diethyl azodicarboxylate
DMF: Dimethyl formamide
DMSO: dimethyl sulfoxide
EtOH: Ethanol
ESI: Electrospray ionisation
FC. Flash chromatography
HPLC: High performance liquid chromatography
MeOH: methanol
MS: Mass spectrometry
NMR: Nuclear magnetic resonance
RedAl: Sodium bis(2-methoxyethoxy)aluminum hydride
tBuOK: Potassium tert-butoxide
TBME: tert-Butyl methyl ether
TFA: Trifluoroacetic acid
THF: Tetrahydrofuran
TLC: Thin layer chromatography
TMSCI: rimethyl chlorosilane General Procedure A: Formylation Under argon at −20° C., to a solution of compound II (1.0 eq.) in dry $CH_2Cl_2$ was added dichloromethylmethyl ether (1.5 eq.). $SnCl_4$ (1.0 eq.) was added dropwise over a period of 30 min, while maintaining the inside temperature at −20° C. After the addition, the mixture was allowed to slowly warm up to room. After disappearance of the starting material (TLC), the reaction mixture was again cooled to −10° C. and quenched by slowl addition of $NaHCO_3$. The organic phase was collected, the aqueous phase was extracted with three portions of tert-butyl methyl ether (TBME), the combined organic phases were washed with brine, dried with $MgSO_4$ and the solvents removed under reduced pressure to give compound III.

Example 1

Methyl 2-formyl-3,4,5-trimethoxybenzoate was obtained as a yellow foam (39.0 g, 90%, 85% HPLC purity) by reacting methyl 3,4,5-trimethoxybenzoate (36.0 g) with dichloromethylmethyl ether (27.0 g, 1.5 eq.) and $SnCl_4$ (41.5 g, 1.0 eq). The product, which is rather unstable, was directly used for the next step.

NMR $CDCl_3$ 300 MHz δ in ppm J in Hz: 10.28 (s, 1H, COH), 6.93 (s, 1H, Ar), 3.96 (s, 3H, OMe), 3.93 (s, 3H, OMe), 3.89 (s, 6H, 2 OMe).

General Procedure B: Demethylation

Under argon at −10°C., to a solution of compound III (1 eq.) in methylene chloride, $BBr_3$ (0.5 eq.) was added over a period of 20 min, such that the temperature was not exceeding 0° C. The mixture was stirred at 0° C., until disappearance of the starting material. The reaction mixture was poured into ice-water and the aqueous layer was extracted with two portions of TBME. The combined organic phases were washed with water, dried with $MgSO_4$, and the solvents evaporated under reduced pressure to give compound IV.

Example 2

Methyl 2-formyl-3-hydroxy-4,5-dimethoxy-benzoate (36.8 g, 98%, 88% HPLC purity) was obtained as a white crystalline compound by reacting methyl 2-formyl-3,4,5-trimethoxybenzoate (39.5 g) with $BBr_3$ (7.5 ml, 0.5 eq.).

NMR $CDCl_3$ 300 MHz δ in ppm J in Hz: 12.28 (s, 1H, OH), 10.26 (s, 1H, COH), 6.57 (s, 1H, Ar), 4.01 (s, 3H, OMe), 3.98 (s, 6H, 2 OMe).

General Procedure C: Synthesis of Benzofurans

Under argon, compound IV (1 eq.) was dissolved in DMF or toluene (Fluka on 4 Å Mol. sieve), $K_2CO_3$ powder (2.4 eq.) and in some cases tetrabuthylammonium bromide (0.1 eq.) was added. After 10 min stirring at r.t., a bromoketone V, a bromomalonic ester VII or a α-bromoester VII (1.2 to 1.9 eq.) was added as well as some 4 Å Mol. sieves. The reaction was stirred 3 h to 24 h at 110° C. The reaction mixture was filtrated and the solvent evaporated. The residual brown oil was dissolved in $CH_2Cl_2$ and washed with water and brine. The organic layer was dried with $MgSO_4$, the solvent evaporated to give the compound VI or VIII.

Example 3

6,7-Dimethoxy-2-cyclopropylcarbonyl-benzofuran-4-carboxylic acid methyl ester (128 mg, 59%) was obtained as a yellow solid after crystallisation from ethyl acetate by reacting methyl 2-formyl-3-hydroxy-4,5-dimethoxy-benzoate (170 mg, 0.70 mmol) with 2-bromo-1-cyclopropylethanone (0.138 g, 0.849 mmol) (which was previously obtained from the reaction of 1-cyclopropyl-vinyloxitrimethylsilane with N-bromosuccinimide), $K_2CO_3$ (170 mg, 1.7 eq.) and tetrabuthylammonium bromide (27 mg, 0.07 mmol)

NMR $CDCl_3$ 300 MHz δ in ppm J in Hz: 7.98 (s, 1H, Ar), 7.68 (m, 1H, Ar), 4.28 (s, 3H, OMe), 3.93 (s, 3H, OMe), 3.92 (s, 3H, OMe), 2.72–2.55 (m, 1H), 1.29–1.25 (m, 2H), 1.09–1.04 (m, 2H).

Example 4

6,7-Dimethoxy-2-phenylcarbonyl-benzofuran-4-carboxylic acid methyl ester (1.1 g, 56%) was obtained as a yellow solid by reacting Methyl 2-formyl-3-hydroxy-4,5-dimethoxy-benzoate (1.5 g, 6.24 mmol) with $K_2CO_3$ powder (2.07 mg, 14.97 mmol) and phenacyl bromide (2.36 mg, 11.86 mmol).

NMR $CDCl_3$ 300 MHz δ in ppm J in Hz: 8.04 (s, 1H, Ar), 7.74 (s, 1H, Ar), 7.68–7.54 (m, 5H, Ar), 4.37 (s, 3H, OMe), 4.00 (s, 3H, OMe), 3.97 (s, 3H, OMe). MP: 116–120° C.

Example 5

6,7-Dimethoxy-2-(2,2-dimethylpropanoyl)-benzofuran-4-carboxylic acid methyl ester (182 mg, 57%) was obtained as a yellow solid by reacting methyl 2-formyl-3-hydroxy-4,5-dimethoxy-benzoate (250 mg, 1.04 mmol) with $K_2CO_3$ powder (338 mg, 2.44 mmol) and 1-bromopinacolon (265 μl, 1.96 mmol).

NMR $CDCl_3$ 300 MHz δ in ppm J in Hz: 8.04 (s, 1H, Ar), 7.72 (s, 1H, Ar), 4.35 (s, 3H, OMe), 3.98 (s, 3H, OMe), 3.96 (s, 3H, OMe), 1.45 (s, 9H, tert-Bu) MP 104–108° C.

Example 6

6,7-Dimethoxy-2-tert-butoxycarbonyl-benzofuran-4-carboxylic acid methyl ester (100 mg, 37%) was obtained as a yellow solid by reacting methyl 2-formyl-3-hydroxy-4,5-dimethoxy-benzoate (200 mg, 0.83 mmol) with $K_2CO_3$ powder (172 mg, 1.24 mmol), tetrabuthylammonium bromide (27 mg, 0.08 mmol) and bromomalonic acid tert-butyl ester (294 mg, 1.00 mmol).

General Procedure D: Reduction of the Ketone

Under argon at 0° C., to a solution of the ketone VI (1 eq.) in freshly distilled THF trimethylsilyl chloride (10 eq.), 4 Å Mol sieve powder and then sodium cyanoborohydride (10 eq.) were added. The reaction was complete after stirring it for 5 h to 24 h at r.t. Dichloromethane was added to the reaction mixture, which was then filtrated through celite. After several washings of the residue with $CH_2Cl_2$, the filtrate was washed with water and brine, dried with $MgSO_4$ and the solvents evaporated to give compound IX.

Example 7

6,7-Dimethoxy-2-cyclopropylmethyl-benzofuran-4-carboxylic acid methyl ester (94 mg, 90%) was obtained as a glassy solid by reacting trimethylsilyl chloride (46 μl, 3.61 mmol) and sodium cyanoborohydride (240 mg, 3.61 mmol). MS ESI: 291 (M+H).

Example 8

6,7-Dimethoxy-2-phenylmethyl-benzofuran-4-carboxylic acid methyl ester (186 mg, 95%) was obtained as a glassy solid, after purification by flash chromatography (Rf 0.66, 3:2, hexane/ethyl acetate) by reacting 6,7-dimethoxy-2-phenylcarbonyl-benzofuran-4-carboxylic acid methyl ester (200 mg, 0.588 mmol) with sodium cyanoborohydride (370 mg, 5.88 mmol) and trimethylsilyl chloride (743 ml, 5.88 mmol).

MS ESI+: 365 (M+K), 349 (M+Na), 327 (M+H), 295 (M−OMe)

NMR $CDCl_3$ 300 MHz δ in ppm J in Hz: 7.56 (s, 1H, Ar), 7.33–7.26 (m, 5H, Ar), 6.91 (s, 1H, Ar), 4.24 (s, 3H, OMe), 4.13 (s, 2H, $CH_2Ar$), 3.93 (s, 3H, OMe), 3.91 (s, 3H, OMe).

Example 9

6,7-Dimethoxy-2-(2,2-dimethylpropyl)-benzofuran-4-carboxylic acid methyl ester (180 mg, 94%) was obtained as a glassy solid by reacting 6,7-dimethoxy-2-(2,2-dimethylpropanoyl)-benzofuran-4-carboxylic acid methyl ester (200 mg, 0.62 mmol) with sodium cyanoborohydride (392 mg, 6.24 mmol) and trimethylsilyl chloride (789 µl, 6.24 mmol).

NMR CDCl$_3$ 300 MHz δ in ppm J in Hz: 7.57 (s, 1H, Ar), 6.92 (s, 1H, Ar), 4.29 (s, 3H, OMe), 3.95 (s, 3H, OMe), 3.94(s, 3H, OMe), 2.66 (s, 2H, CH$_2$), 1.03 (s, 9H, tert-Bu)

General Procedure E: Alternative Route to Obtain Benzofuran Derivatives IX

Compound XI (1 eq.) was reacted with compound XII (1 eq.) (obtained by sodium borohydride reduction of the corresponding ketone) as described previously (Wipf, P.; Weiner, W. S. *J. Org. Chem.* 1999, 64, 5321–5324) to give compound XIII.

Example 10

3-(1-Cyclopropyl-trimethylsilylprop-2-ynyloxy)-4,5-dimethoxy-benzoic acid methyl ester was obtained as a colorless oil in 60% yield from 1-cyclopropyl-3-(trimethylsilyl)prop-2yn-1-ol. The same compound can also be obtained by a copper-1 (CuCl)-catalyzed process as described by Godfrey et al.(Godfrey Jr., J. D. et al, *Tetrahedron Lett.* 1994, 35, 6405–6408).

MS: M$^+$362.

Ether XIII (1 eq.), K$_2$CO$_3$ (3 eq.) and KF (3 eq.) were dissolved in methanol. The mixture was stirred and the reaction was monitored by TLC. After 25 minutes the reaction was complete and the mixture was partitioned between of water and a mixture of hexane/ethyl acetate 4:1. The layers were separated, the aqueous layer was washed three times with of hexane/ethyl acetate 4:1. The organic layers were combined and evaporated to give the resulting acetylene which was used directly for the next step.

Example 11

3-(1-Cyclopropyl-prop-2-ynyloxy)-4,5-dimethoxy-benzoic acid methyl ester (17.5 g, 71%) was obtained as a white solid by crystallization from hexane/ether by reacting 3-(1-cyclopropyl-trimethylsilylprop-2-ynyloxy)-4,5-dimethoxy-benzoic acid methyl ester (30.87 g, 80 mmol) with K$_2$CO$_3$ (30 g) and KF (30 g) 17.5 g, 60.4 mmol, 71%.

mp. 93–94° C.

The acetylene previously obtained (1 eq.) was dissolved in DMF (tech.) containing 5% N,N-diethylaniline and the reaction mixture was stirred for 2 h at 150° C. After work-up and crystallisation from ether the compound IX was obtained.

Example 12

6,7-Dimethoxy-2-cyclopropylmethyl-benzofuran-4-carboxylic acid methyl ester (50%) was obtained as white-red crystals by reacting in an intramolecular fashion 3-(1-cyclopropyl-prop-2-ynyloxy)-4,5-dimethoxy-benzoic acid methyl ester (88 g, 0.316 mol)

NMR CDCl$_3$ 300 MHz δ in ppm J in Hz: 7.57 (s, 1H, Ar), 7.00 (m, 1H, Ar), 4.28 (s, 3H, OMe), 3.95 (s, 3H, OMe), 3.94 (s, 3H, OMe), 2.70 (d, 2H, J=6.6), 1.95–1.75 (m, 1H), 0.62–0.59 (m, 2H), 0.29–0.25 (m, 2H).

General Procedure F: Reduction of the Ester to Alcohol

Under argon, ester XIV (1 eq.) was dissolved in THF freshly distilled and treated with LiAlH$_4$ (3 eq.) The reaction was stirred at 60° C. for 2 h until disappearance of the starting material. The reaction was quenched with 0.5 N HCl, the white precipitate filtrated and washed with ether. The organic layer was dried with MgSO$_4$ and the solvents evaporated to give the alcohol XV.

Example 13

(6,7-Dimethoxy-2-phenylmethyl-benzofuran-4-yl)-methanol (82 mg, 90%) was obtained by reacting 6,7-dimethoxy-2-phenylmethyl-benzofuran-4-carboxylic acid methyl ester (100 mg, 0.30 mmol) with LiAlH$_4$ (33 mg, 0.91 mmol).

MS ESI: 321 (M+Na).

General Procedure G: Oxidation of the Alcohol to Aldehyde

Under argon, alcohol XV (1 eq.) was dissolved in dichloromethane and MnO$_2$ (10 eq.) was added. The reaction mixture was stirred 3 h at r.t. and filtrated over celite. The celite was washed with excess of CH$_2$Cl$_2$, the solvent evaporated to give the aldehyde XVI.

Example 14

6,7-Dimethoxy-2-phenylmethyl-benzofuran-4-carbaldehyde (119 mg, 62%) was obtained as an oil by reacting (6,7-dimethoxy-2-phenylmethyl-benzofuran-4-yl)-methanol (192 mg, 1.29 mmol) with MnO$_2$ (1.121 g, 12.90 mmol)

General Procedure H: Reduction of the Ester to the Aldehyde

Under argon at 0° C., to a solution of sodium dihydrobis(2-methoxyethoxy)-aluminate (Red Al, ca. 3.5 M in toluene) (3.1 eq.) in toluene (over 4 Å Mol. sieve) was added dropwise, within 30 min, morpholine (3.4 eq.) in toluene. The resulting solution was stirred for 30 min, and it was slowly added at −30° C. to a solution of the ester XIV (1 eq.) in toluene. The reaction mixture was then stirred for 4 h at −15° C. and quenched by addition of 3N NaOH and stirred until it reached r.t. The reaction mixture was then diluted with ice water and extracted with toluene. The organic layer was washed with water, dried over MgSO$_4$ and the solvent evaporated to give compound XVI.

Example 15

6,7-Dimethoxy-2-cyclopropylmethyl-benzofuran-4-carbaldehyde (1.16 g, 66%) was obtained as light yellow crystals after crystallisation in 5:1 ethyl acetate/hexane by reacting sodium dihydro-bis(2-methoxyethoxy)-aluminate (Red Al, ca. 3.5M in toluene) (6.5 ml, 22.6 mmol) with morpholine (2.1 ml, 24.0 mmol) and 6,7-dimethoxy-2-cyclopropylmethyl-benzofuran-4-carboxylic acid methyl ester (2.05 g, 7.0 mmol)

NMR CDCl$_3$ 300 MHz δ in ppm J in Hz: 10.06 (s, 1H, COH), 7.32 (s, 1H, Ar) 7.51 (s, 1H, Ar), 4.35 (s, 3H, OMe), 3.97 (s, 3H, OMe), 2.72 (d, 2H, J=7.1), 1.19–1.17 (m, 1H), 0.64–0.60 (m, 2H), 0.29–0.27 (m, 2H). MP 44–46° C.

Example 16

6,7-Dimethoxy-2-(2,2dimethlypropyl)-benzofuran-4-carbaldehyde (115 mg, 80%) was obtained as an oil from the reaction of sodium dihydro-bis(2-methoxyethoxy)-aluminate (Red Al, ca. 3.5M in toluene) (500 µl, 1.62 mmol) with morpholine (159 µl, 1.83 mmol) and 6,7-dimethoxy-2-(2,2dimethlypropyl)-benzofuran-4-carboxylic acid methyl ester (160 mg, 0.522 mmol).

General Procedure I: Coupling With Anilinopropionitrile

Under argon at 10° C., the aldehyde XVI (1 eq.) was dissolved in DMSO (25 ml) and freshly crystallized 3-anilinopropionitrile (1.1 eq.) was added. Potassium tert-butoxide (1.15 eq.) was added in portions to the reaction mixture. The solution was stirred at 10° C. for 1 h and at r.t. for 3 h. The reaction mixture was poured into ice-water and extracted 3 times with ethyl acetate. The organic layer was washed with water and dried over $MgSO_4$. The solvents were evaporated to give compound XVII.

Example 17

3-Anilino-2-(6,7-dimethoxy-2-cyclopropylmethyl-benzofuran-4-ylmethyl)-acrylonitrile (1.87 g, 49%) was obtained after purification by flash chromatography 2:3 ethyl acetate/hexane to as a yellow oil from the reaction of 6,7-dimethoxy-2-cyclopropylmethyl-benzofuran-4-carbaldehyde (2.6 g, 9.9 mmol) with 3-anilinopropionitrile (1.44 g, 10.9 mmol) and potassium tert-butoxide (1.28 g, 11.5 mmol)

Example 18

3-Anilino-2-(6,7-dimethoxy-2-phenylmethyl-benzofuran-4-ylmethyl)-acrylonitrile (88 mg, 53%) was obtained after purification by flash chromatography (2:3 ethyl acetate/hexane) as a yellow oil by reacting of 6,7-dimethoxy-2-phenylmethyl-benzofuran-4-carbaldehyde (119 mg, 0.40 mmol) with 3-anilinopropionitrile (58 mg, 0.44 mmol) and potassium tert-butoxide (52 mg, 0.46 mmol)

MS ESI: 423 (M–H).

Example 19

3-Anilino-2-(6,7-dimethoxy-2-(2,2-dimethlypropyl)-benzofuran-4-ylmethyl)-acrylonitrile (91 mg, 54%) was obtained after purification by flash chromatography (2:3 ethyl acetate/hexane) as a yellow oil by reacting 6,7-dimethoxy-2-(2,2dimethylpropyl)-benzofuran-4-carbaldehyde (115 mg, 0.42 mmol) with 3-anilinopropionitrile (60 mg, 0.46 mmol) and potassium tert-butoxide (54 mg, 0.48 mmol)

MS ESI: 427 (M+Na).

General Procedure J: Cyclisation With Guanidine

Under argon, to a solution of guanidine hydrochloride (3 eq.) in ethanol potassium tert-butoxide (3 eq.) was added and the mixture was stirred for 15 min. The fine precipitate was filtered through celite under argon and the filtrate was added to a solution of compound XVII (1 eq.) in ethanol. The reaction mixture was stirred under reflux conditions for 8 h. After cooling the reaction to r.t., then to −20° C. compound I precipitated.

Example 20

5-(2-Cyclopropylmethyl-6,7-dimethoxy-benzofuran-4-ylmethyl)-pyrimidine-2,4-diamine (1.16 g, 96%) was obtained as a white-yellow precipitate by reacting guanidine hydrochloride (1.37 g, 14.44 mmol), potassium tert-butoxide (1.62 g, 14.44 mmol) and 3-anilino-2-(6,7-dimethoxy-2-cyclopropylmethyl-benzofuran-4-ylmethyl)acrylonitrile (1.87 g, 4.81 mmol)

NMR $CD_3OD$ 500 MHz δ in ppm J in Hz: 6.95–7.35 (m, 1H, Ar), 6.78 (s, 1H, Ar) 6.44 (s, 1H, Ar), 4.03 (s, 3H, OMe), 3.85 (s, 3H, OMe), 3.81 (s, 2H, $CH_2$), 2.66 (d, 2H, J=6.8), 1.14–1.04 (m, 1H), 0.59–0.54 (m, 2H), 0.28–0.25 (m, 2H).

MS ISP: 397 (M+Na, 25%), 355 (M+H, 100%); HPLC purity RP $C_{18}$ Dicovery: 98%.

Example 21

5-(2-Benzyl-6,7-dimethoxy-benzofuran-4-ylmethyl)-pyrimidine-2,4-diamine (20 mg, 36%) was obtained as a white-yellow precipitate by reacting guanidine hydrochloride (40 mg, 0.42 mmol), potassium tert-butoxide (47 mg, 0.42 mmol) and 3-anilino-2-(6,7-dimethoxy-2-phenylmethyl-benzofuran-4-ylmethyl)-acrylonitrile (59 mg, 0.14 mmol)

MS ESI: 391 (M+H); HPLC purity RP $C_{18}$ Dicovery: 97%.

Example 22

5-(6,7-Dimethoxy-2-(2,2-dimethlypropyl)-benzofuran-4-ylmethyl)-pyrimidine-2,4-diamine (28 mg, 33%) was obtained as a white-yellow precipitate by reacting guanidine hydrochloride (64 mg, 0.67 mmol), potassium tert-butoxide (75 mg, 0.67 mmol) and 3-anilino-2-(6,7-dimethoxy-2-(2,2-dimethlypropyl)-benzofuran-4-ylmethyl)-acrylonitrile (91 mg, 0.22 mmol)

MS ESI: 371 (M+H); HPLC purity RP $C_{18}$ Dicovery: 99%.

Example 23

Following general procedure C, 2-(biphenyl-4-carboyl)-6,7-dimethoxy-benzofuran-4-carboxylic acid methyl ester (1.6 g, 95%) was obtained as a yellow solid by reacting methyl 2-formyl-3-hydroxy-4,5-dimethoxy-benzoate (1.0 g, 4.16 mmol) with $K_2CO_3$ powder (1.44 mg, 10.4 mmol) and 4-phenyl-phenacylbromid (2.29 g, 8.32 mmol).

Example 24

Following general procedure C, 6,7-dimethoxy-2-(4-methoxy-benzoyl)-benzofuran-4-carboxylic acid methyl ester (0.331 g, 43%) was obtained as a yellow solid by reacting methyl 2-formyl-3-hydroxy-4,5-dimethoxy-benzoate (0.5 g, 2.08 mmol) with $K_2CO_3$ powder (0.69 mg, 4.9 mmol) and 2-bromo-4-methoxyacetopenon (0.98 g, 4.16 mmol)

NMR $CDCl_3$ 300 MHz δ in ppm J in Hz: 8.01 (d, 2H, Ar), 7.92 (s, 1H, Ar), 7.64 (s, 1H, Ar), 6.94 (d, 2H, Ar), 4.27 (s, 3H, OMe), 3.93 (s, 3H, OMe), 3.90 (s, 3H, OMe), 3.83 (s, 3H, OMe).

Example 25

Following general procedure C, 2-(4-fluoro-benzoyl)-6,7-dimethoxy-benzofuran-4-caboxylic acid methyl ester (2.37, 82%) was obtained as a yellow solid by reacting methyl 2-formyl-3-hydroxy-4,5-dimethoxy-benzoate (2.0 g, 8.32 mmol) with $K_2CO_3$ powder (2.30 mg, 16.62 mmol) and 2-bromo-4-fluoracetopenon (2.71 g, 12.49 mmol).

Example 26

Following general procedure D, 2-biphenyl-4-ylmethyl-6,7-dimethoxy-benzofuran-4-carboxylic acid methyl ester (474 mg, 98%) was obtained as yellow oil by reacting trimethylsilyl chloride (1.52 ml, 12.0 mmol) and sodium cyanoborohydride (754 mg, 12.0 mmol).

Example 27

Following general procedure D, 6,7-dimethoxy-2-(4-methoxy-benzyl)-benzofuran-4-carboxylic acid methyl ester (131 mg, 93%) was obtained as yellow oil by reacting trimethylsilyl chloride (0.341 ml, 2.7 mmol) and sodium cyanoborohydride (169 mg, 2.7 mmol).

MS ESI 1: 379 (M+Na).

Example 28

Following general procedure D, 2-(4-fluoro-benzyl)-6,7-dimethoxy-benzofuran-4-carboxylic acid methyl ester (868 mg, 90%) was obtained as yellow oil by reacting trimethylsilyl chloride (3.64 ml, 28.7 mmol) and sodium cyanoborohydride (1.8 g, 28.7 mmol).

MS ESI+329 (M–Me).

Example 29

Cleavage of the tBu Ester

Under argon at 0° C. 6,7-Dimethoxy-benzofuran-2,4-dicarboxylic acid 2-tert-butyl ester 4-methyl ester (10 g, 29.7 mmol) was dissolved in TFA (23 ml, 297.3 mmol) and the reaction mixture was stirred for 3 h allowing the temperature to reach r.t. The excess of TFA was evaporated and the resulting pink solid was triturated in ether. The resulting solid was dissolved in NaHCO$_3$ saturated solution, the aqueous layer was extracted with ether then the basic aqueous solution was acidified to pH=1 with 6N HCl and the product was extracted with ethyl acetate. The ethyl acetate organic layer was washed with brine, dried over MgSO$_4$ and the solvent evaporated to give 6,7-dimethxy-benzofuran-2,4-dicarboxylic acid 4-methyl ester (6.43, 77%) as a white solid.

MS ESI–279 (M–H).

General Procedure K: Coupling With Amines

Under argon at 0° C., to a solution of the acid 6,7-Dimethxy-benzofuran-2,4-dicarboxylic acid 4-methyl ester (1 eq.) in CH$_2$Cl$_2$/DMF (20:1) were added HOBt (1.2 eq.), EDC(1.2 eq.), the secondary or primary amine (1.1 eq.) and finally triethyl amine (3eq.). The reaction mixture was stirred overnight. Some additional CH$_2$Cl$_2$ was added and the organic layer was washed with HCl 1N, H$_2$O, NaHCO$_3$ sat and brine. After drying the organic layer over MgSO4 the solvent was evaporated to give compound IX.

Example 30

2-Dimethylcarbamoyl-6,7-dimethoxy-benzofuran-4-carboxylic acid methyl ester (1.64 g, 97%) was obtained by reacting give 6,7-dimethxy-benzofuran-2,4-dicarboxylic acid 4-methyl ester (1.5 g, 5.35 mmol) with HOBt (868 mg, 6.42 mmol) EDC (1.23 g, 6.42 mmol), dimethylamine (480 mg, 5.88 mmol), and Et$_3$N (2.23 ml, 16.05 mmol).

MS ESI+: 308 (M+H).

Example 31

2-(3,4-Dihydro-1H-isoquinoline-2-carbonyl)-6,7-dimethoxy-benzofuran-4-carboxylic acid methyl ester (2.09 g, 98%) was obtained by reacting give 6,7-dimethxy-benzofuran-2,4-dicarboxylic acid 4-methyl ester (1.5 g, 5.35 mmol) with HOBt (868 mg, 6.42 mmol) EDC (1.23 g, 6.42 mmol), tetrahydrosisoquinoline (0.747 ml, 5.88 mmol), and Et$_3$N (2.23 ml, 16.05 mmol).

MS ESI+: 396 (M+H).

Example 32

6,7-Dimethoxy-2-(morpholine-4-carbonyl)-benzofuran-4-carboxylic acid methyl ester (1.85 g, 98%) was obtained by reacting give 6,7-dimethxy-benzofuran-2,4-dicarboxylic acid 4-methyl ester (1.5 g, 5.35 mmol) with HOBt (868 mg, 6.42 mmol) EDC (1.23 g, 6.42 mmol), morpholine (0.513 ml, 5.88 mmol), and Et$_3$N (2.23 ml, 16.05 mmol).

MS ESI+: 350 (M+H).

Example 33

2-(4-Fluoro-phenylcarbamoyl)-6,7-dimethoxy-benzofuran-4-carboxylic acid methyl ester (978 mg, 52%) was obtained by reacting give 6,7-dimethxy-benzofuran-2,4-dicarboxylic acid 4-methyl ester (1.4 g, 4.99 mmol) with HOBt (810 mg, 5.99 mmol) EDC (1.15 g, 5.99 mmol), 4-fluoroaniline (0.527 ml, 5.49 mmol), and Et$_3$N (2.1 ml, 14.98 mmol).

MS ESI–:372 (M+H).

Example 34

Reduction of the Acid

Under argon, 6,7-dimethxy-benzofuran-2,4-dicarboxylic acid 4-methyl ester (66.46 g, 237 mmol) was dissolved in THF dist. and a 2M solution of BH$_3$.DMS (116 ml, 0.260 mmol) was slowly added. The reaction mixture was stirred at reflux overnight. After cooling to r.t the reaction was quenched with MeOH. The solvents were then evaporated and the resulting oil was dissolved in ethyl acetate. The organic layer was washed with NaHCO$_3$ sat., H$_2$O and brine, dried over MgSO$_4$. 2-Hydroxymethyl-6,7-dimethoxy-benzofuran-4-carboxylic acid methyl ester (34 g, 54%) was obtained as yellow-white solid after purification by FC Hexane/ethyl acetate (3:2).

MS ESI+:267 (M+H).

General Procedure L: Coupling with Halogen Derivatives

Under argon, to a solution of 2-hydroxymethyl-6,7-dimethoxy-benzofuran-4-carboxylic acid (1 eq.) in DMF dried over molecular sieve was added portionwise NaH 60% (1.1 eq.). Halogen derivatives XR$^9$ (1.05 eq.) were slowly added to the solution. The reaction was stirred 1 h at r.t and was quenched with some H$_2$O. After evaporation of the DMF the resulting oil was partitioned between ethyl acetate and NaHCO$_3$. After extraction of the water layer with ethyl acetate the organic layer was washed with H$_2$O, KHSO$_4$ 1N and brine, dried over MgSO$_4$ and the solvents evaporated. The pure compound IX was obtained after purification by FC hexane/ethyl acetate (4:1).

Example 35

2-Allyloxymethyl-6,7-dimethoxy-benzofuran-4-carboxylic acid methyl ester (10.43 g, 60%) was obtained as a yellow oil by reacting 2-hydroxymethyl-6,7-dimethoxy-benzofuran-4-carboxylic acid (15 g, 56.39 mmol) with NaH 60% (2.48 g, 62.03 mmol) and allyl bromide (5.01 ml, 59.21 mmol).

LC MS clean but no ionisation.

Example 36

6,7-Dimethoxy-2-(4-methoxy-benzyloxymethyl)-benzofuran-4-carboxylic acid methyl ester (480 mg, 40%) was obtained as a crystalline solid by reacting 2-hydroxymethyl-6,7-dimethoxy-benzofuran-4-carboxylic acid (840 mg, 3.15 mmol) with NaH 60% (139 mg, 3.47 mmol), $K_2CO_3$ (436 mg, 3.15 mmol) and methoxybenzyl chloride (0.449 ml, 3.31 mmol).

NMR $CDCl_3$ 300 MHz □ in ppm J in Hz: 7.61 (s, 1H, Ar), 7.29 (d, 2H, Ar), 7.21 (s, 1H, Ar), 6.28 (d, 2H, Ar), 4.61 (s, 2H, $CH_2$), 4.56 (s, 2H, $CH_2$), 4.28 (s, 3H, OMe), 3.93 (s, 6H, 2×OMe), 3.80 (s, 3H, OMe).

Example 37

Following general procedure F, (2-biphenyl-4-ylmethyl-6,7-dimethoxy-benzofuran-4-yl)-methanol (395 mg, 90%) was obtained as a trasparant oil by reacting 2-biphenyl-4-ylmethyl-6,7-dimethoxy-benzofuran-4-carboxylic acid methyl ester (474 mg, 1.18 mmol) with $LiAlH_4$ (135 mg, 3.53 mmol).

MS ESI+: 357 (M−OH).

Example 38

Following general procedure F, [6,7-dimethoxy-2-(4-methoxy-benzyl)-benzofuran-4-yl]-methanol (79 mg, 66%) was obtained as an oil by reacting 6,7-dimethoxy-2-(4-methoxy-benzyl)-benzofuran-4-carboxylic acid methyl ester (131 mg, 0.36 mmol) with $LiAlH_4$ (28 mg, 0.73 mmol).

MS ESI+:311 (M−OH).

Example 39

Following general procedure F, [2-(4-fluoro-benzyl)-6,7-dimethoxy-benzofuran-4-yl]-methanol (709 mg, 86%) was obtained as an oil by reacting 2-(4-fluoro-benzyl)-6,7-dimethoxy-benzofuran-4-carboxylic acid methyl ester (868 mg, 2.60 mmol) with $LiAlH_4$ (197 mg, 5.21 mmol).

MS ESI+: 299 (M−OH).

Example 40

Following general procedure F, (2-dimethylaminomethyl-6,7-dimethoxy-benzofuran-4-yl)-methanol (507 g, 60%) was obtained as an oil by reacting 2-dimethylcarbamoyl-6,7-dimethoxy-benzofuran-4-carboxylic acid methyl ester (1.0 g, 2.60 mmol) with $LiAlH_4$ (494 mg, 13.01 mmol).

MS ESI+: 266 (M+H).

Example 41

Following general procedure F, [2-(3,4-dihydro-1H-isoquinolin-2-ylmethyl)-6,7-dimethoxy-benzofuran-4-yl]-methanol (970 mg, 77%) was obtained as an oil by reacting 2-(3,4-dihydro-1H-isoquinoline-2-carbonyl)-6,7-dimethoxy-benzofuran-4-carboxylic acid methyl ester (1.4 g, 3.54 mmol) with $LiAlH_4$ (537 mg, 14.16 mmol).

MS ESI+: 354 (M+H).

Example 42

Following general procedure F, (6,7-dimethoxy-2-morpholin-4-ylmethyl-benzofuran-4-yl)-methanol (800 mg, 60%) was obtained as an oil by reacting 6,7-dimethoxy-2-(morpholine-4-carbonyl)-benzofuran-4-carboxylic acid methyl ester (1.52 g, 4.35 mmol) with $LiAlH_4$ (660 mg, 17.40 mmol).

MS ESI+:308 (M+H).

Example 43

Following general procedure F, {2-[(4-fluoro-phenylamino)-methyl]-6,7-dimethoxy-benzofuran-4-yl}-methanol (724 mg, 84%) was obtained as an oil by reacting 2-(4-fluoro-phenylcarbamoyl)-6,7-dimethoxy-benzofuran-4-carboxylic acid methyl ester (974 mg, 2.6 mmol) with $LiAlH_4$ (495 mg, 13.0 mmol).

MS ESI+: 330 (M+H) very weak signal.

Example 44

Following general procedure F, (2-allyloxymethyl-6,7-dimethoxy-benzofuran-4-yl)-methanol (1.76 g, 98%) was obtained as an oil by reacting 2-allyloxymethyl-6,7-dimethoxy-benzofuran-4-carboxylic acid methyl ester (1.95 g, 6.36 mmol) with $LiAlH_4$ (483 mg, 12.73 mmol).

MS ESI+: 261 (M−OH).

Example 45

Following general procedure F, [6,7-dimethoxy-2-(4-methoxy-benzyloxymethyl)-benzofuran-4-yl]-methanol (390 mg, 95%) was obtained as an oil by reacting 6,7-dimethoxy-2-(4-methoxy-benzyloxymethyl)-benzofuran-4-carboxylic acid methyl ester (445 mg, 1.15 mmol) with $LiAlH_4$ (87 mg, 2.30 mmol).

MS ESI+: 341 (M−OH).

Example 46

Following general procedure F, (6,7-dimethoxy-2-phenyl-benzofuran-4-yl)-methanol (150 mg, 74%) was obtained as an oil by reacting 6,7-dimethoxy-2-phenylbenzofuran-4-carboxylic acid methyl ester (235 mg, 0.735 mmol) with $LiAlH_4$ (14 mg, 0.377 mmol). 6,7-dimethoxy-2-phenylbenzofuran-4-carboxylic acid methyl ester (240 mg, 22%) was obtained following the palladium coupling procedure [J. Org. Chem. 1996, 61, 9280–9288; Bioorg. Med. Chem., 1999, 7, 6, 1131–1140] by reacting 2-bromo-3-hydroxy-4,5-dimethoxy-benzoic acid methyl ester (1 g, 3.44 mmol) (P. Wipf and W. S. Weiner, J. Org. Chem. 1999, 64, 5321–5324) with phenylacetylen (525 mg, 5.15 mmol), CuI (13 mg, 0.07 mmol) and $Pd(PPh_3)Cl_2$ (24 mg, 0.04 mmol) in $Et_3N$/DMF (3:1).

MS ESI+: 267 (M−OH).

Example 47

Following general procedure F, [6,7-dimethoxy-2-(2-phenyl-[1,3]dioxolan-2-yl)-benzofuran-4-yl]-methanol (3.94 g, 98%) was obtained as an oil by 6,7-dimethoxy-2-(2-phenyl-[1,3]dioxolan-2-yl)-benzofuran-4-carboxylic acid methyl ester (4.29 g, 11.16 mmol) with $LiAlH_4$ (980 mg, 24.5 mmol).

MS ESI+: 357 (M+H).

Example 48

Following general procedure G, 2-biphenyl-4-ylmethyl-6,7-dimethoxy-benzofuran-4-carbaldehyde (105 mg, 27%) was obtained as a solid by reacting (2-biphenyl-4-ylmethyl- 6,7-dimethoxy-benzofuran-4-yl)-methanol (395 mg, 1.06 mmol) with MnO$_2$ (1.73 g, 19.9 mmol)

MS ESI+: 373 (M+H).

Example 49

Following general procedure G, 6,7-dimethoxy-2-(4-methoxy-benzyl)-benzofuran-4-carbaldehyde (20 mg, 25%) was obtained as am oil by reacting [6,7-dimethoxy-2-(4-methoxy-benzyl)-benzofuran-4-yl]-methanol (79 mg, 0.24 mmol) with MnO$_2$ (210 g, 2.42 mmol)

MS ESI+: 329 (M+H).

Example 50

Following general procedure G, 2-(4-fluoro-benzyl)-6,7-dimethoxy-benzofuran-4-carbaldehyde (396 mg, 56%) was obtained as an oil by reacting [2-(4-fluoro-benzyl)-6,7-dimethoxy-benzofuran-4-yl]-methanol (709 mg, 2.24 mmol) with MnO$_2$ (1.948 g, 22.41 mmol)

MS ESI+: 315 (M+H).

Example 51

Following general procedure G, 2-dimethylaminomethyl-6,7-dimethoxy-benzofuran-4-carbaldehyde (496 mg, 77%) was obtained as a brawn oil by reacting (2-dimethylaminomethyl-6,7-dimethoxy-benzofuran-4-yl)-methanol (500 mg, 1.88 mmol) with MnO$_2$ (1.64 g, 18.84 mmol)

MS ESI+: 264 (M+H).

Example 52

Following general procedure G, 2-(3,4-dihydro-1H-isoquinolin-2-ylmethyl)-6,7-dimethoxy-benzofuran-4-carbaldehyde (638 mg, 71%) was obtained as a brown oil by reacting [2-(3,4-dihydro-1H-isoquinolin-2-ylmethyl)-6,7-dimethoxy-benzofuran-4-yl]-methanol (907 mg, 2.56 mmol) with MnO$_2$ (2.23 g, 25.66 mmol)

MS ESI+: 352 (M+H).

Example 53

Following general procedure G, 6,7-Dimethoxy-2-morpholin-4-ylmethyl-benzofuran-4-carbaldehyde (489 mg, 64%) was obtained as an orange oil by reacting (6,7-dimethoxy- 2-morpholin-4-ylmethyl-benzofuran-4-yl)-methanol (765 mg, 2.49 mmol) with MnO$_2$ (2.16 g, 24.89 mmol)

MS ESI+: 306 (M+H).

Example 54

Following general procedure G, 2-[(4-fluoro-phenylamino)-methyl]-6,7-dimethoxy-benzofuran-4-carbaldehyde (197 mg, 28%) was obtained as an oil by reacting {2-[(4-fluoro-phenylamino)-methyl]-6,7-dimethoxy-benzofuran-4-yl}-methanol (718 mg, 2.16 mmol) with MnO$_2$ (1.88 g, 21.6 mmol)

MS ESI+: 330 (M+H).

Example 55

Following general procedure G, 2-allyloxymethyl-6,7-dimethoxy-benzofuran-4-carbaldehyde (2.01 g, 72%) was obtained as an oil by reacting (2-allyloxymethyl-6,7-dimethoxy-benzofuran-4-yl)-methanol (2.82, 10.17 mmol) with MnO$_2$ (8.80 g, 101.69 mmol)

MS ESI+: 277 (M+H).

Example 56

Following general procedure G, 6,7-dimethoxy-2-(4-methoxy-benzyloxymethyl)-benzofuran-4-carbaldehyde (244 mg, 72%) was obtained as an oil solid by reacting [6,7-dimethoxy-2-(4-methoxy-benzyloxymethyl)-benzofuran-4-yl]-methanol (341 mg, 0.95 mmol) with MnO$_2$ (0.827 g, 9.51 mmol)

MS ESI+: 357 (M+H).

Example 57

Following general procedure G, 6,7-dimethoxy-2-phenyl-benzofuran-4-carbaldehyde (121 mg, 81%) was obtained as an oil by reacting (6,7-dimethoxy-2-phenyl-benzofuran-4-yl)-methanol (150 mg, 0.53 mmol) with MnO$_2$ (467 mg, 5.33 mmol)

MS ESI+: 283 (M+H).

Example 58

Following general procedure G, 6,7-dimethoxy-2-(2-phenyl-[1,3]dioxolan-2-yl)-benzofuran-4-carbaldehyde (3.50 g, 97%) was obtained as a oil by reacting ([6,7-dimethoxy-2-(2-phenyl-[1,3]dioxolan-2-yl)-benzofuran-4-yl]-methanol (3.65 mg, 10.24 mmol) with MnO$_2$ (9.8 g, 102 mmol)

MS ESI+: 355 (M+H).

Example 59

Following general procedure I, 2-(2-biphenyl-4-ylmethyl-6,7-dimethoxy-benzofuran-4-ylmethyl-3-phenylamino-acrylonitrile (58 mg, 41%) was obtained after purification by flash chromatography 2:3 ethyl acetate/hexane as a yellow oil from the reaction of 2-biphenyl-4-ylmethyl-6,7-dimethoxy-benzofuran-4-carbaldehyde (1 05 mg, 0.28 mmol) with 3-anilinopropionitrile (45 mg, 0.30 mmol) and potassium tert-butoxide (36.4 mg, 0.32 mmol).

Example 60

Following general procedure I, 2-[6,7-dimethoxy-2-(4-methoxy-benzoyl)-benzofuran-4-ylmethyl]-3-phenylamino-acrylonitrile which was used for the next step without further purification, was obtained from the reaction 6,7-dimethoxy-2-(4-methoxy-benzyl)-benzofuran-4-carbaldehyde(20 mg, 0.06 mmol) with 3-anilinopropionitrile (9 mg, 0.06 mmol) and potassium tert-butoxide (8 mg, 0.07 mmol).

Example 61

Following general procedure I, 2-[2-(4-fluoro-benzyl)-6, 7-dimethoxy-benzofuran-4-ylmethyl]-3-phenylamino-acrylonitrile which was used for the next step without further purification, was obtained from the reaction 2-(4-fluoro-benzyl)-6,7-dimethoxy-benzofuran-4-carbaldehyde (395 mg, 1.25 mmol) with 3-anilinopropionitrile (200 mg, 1.38 mmol) and potassium tert-butoxide (170 mg, 1.50 mmol)

MS ESI−: 441 (M−H).

Example 62

Following general procedure I, 2-(2-dimethylaminomethyl-6,7-dimethoxy-benzofuran-4-ylmethyl)-3-phenylamino-acrylonitrile which was used for the next step without further purification, was obtained from the 2-dimethylaminomethyl-6,7-dimethoxy-benzofuran-4-carbaldehyde (350 mg, 1.33 mmol) with 3-anilinopropionitrile (223 mg, 1.53 mmol) and potassium tert-butoxide (179 mg, 1.60 mmol)

MS ESI−: 390 (M−H).

Example 63

Following general procedure I, 2-[2-(3,4-dihydro-1H-isoquinolin-2-ylmethyl)-6,7-dimethoxy-benzofuran-4-ylmethyl]-3-phenylamino-acrylonitrile (414 mg, 52%) was obtained after purification by flash chromatography 2:3 ethyl acetate/hexane as a yellow oil from the reaction of 2-2-(3,4-dihydro-1H-isoquinolin-2-ylmethyl)-6,7-dimethoxy-benzofuran-4-carbaldehyde (584 mg, 1.66 mmol) with 3-anilinopropionitrile (279 mg, 1.91 mmol) and potassium tert-butoxide (224 mg, 1.99 mmol)

MS ESI+: 480 (M+H).

Example 64

Following general procedure I, 2-(6,7-dimethoxy-2-morpholin-4-ylmethyl-benzofuran-4-ylmethyl)-3-phenylamino-acrylonitrile (348 mg, 50%) was obtained after purification by flash chromatography 2:3 ethyl acetate/hexane as a yellow oil from the reaction of 6,7-dimethoxy-2-morpholin-4-ylmethyl-benzofuran-4-carbaldehyde (485 mg, 1.59 mmol) with 3-anilinopropionitrile (267 mg, 1.82 mmol) and potassium tert-butoxide (214 mg, 1.90 mmol)

MS ESI+: 434 (M+H).

Example 65

Following general procedure I, 2-{2-[(4-fluoro-phenylamino)-methyl]-6,7-dimethoxy-benzofuran-4-ylmethyl}-3-phenylamino-acrylonitrile which was used for the next step without further purification, was obtained from the 2-[(4-fluoro-phenylamino)-methyl]-6,7-dimethoxy-benzofuran-4-carbaldehyde (197 mg, 0.60 mmol) with 3-anilinopropionitrile (100 mg, 0.69 mmol) and potassium tert-butoxide (80 mg, 0.72 mmol).

Example 66

Following general procedure I, 2-[6,7-dimethoxy-2-(4-methoxy-benzyloxymethyl)-benzofuran-4-ylmethyl]-3-phenylamino-acrylonitrile (123 mg, 38%) was obtained after purification by flash chromatography 2:3 ethyl acetate/hexane as a yellow oil from the reaction of 6,7-dimethoxy-2-(4-methoxy-benzyloxymethyl)-benzofuran-4-carbaldehyde (236 mg, 0.66 mmol) with 3-anilinopropionitrile (106 mg, 0.78 mmol) and potassium tert-butoxide (85 mg, 0.761 mmol)

MS ESI−: 472 (M−H).

Example 67

Following general procedure I, 2-(2-allyloxymethyl-6,7-dimethoxy-benzofuran-4-ylmethyl)-3-phenylamino-acrylonitrile (501 mg, 54%) was obtained after purification by flash chromatography 2:3 ethyl acetate/hexane as a yellow oil from the reaction of 2-allyloxymethyl-6,7-dimethoxy-benzofuran-4-carbaldehyde (626 mg, 2.26 mmol) with 3-anilinopropionitrile (364 mg, 2.49 mmol) and potassium tert-butoxide (292 mg, 2.60 mmol)

MS ESI−: 403 (M−H).

Example 68

Following general procedure I, 2-(6,7-dimethoxy-2-phenyl-benzofuran-4-ylmethyl)-3-phenylamino-acrylonitrile which was used for the next step without further purification, was obtained from the 6,7-dimethoxy-2-phenyl-benzofuran-4-carbaldehyde (120 mg, 0.426 mmol) with 3-anilinopropionitrile (62 mg, 0.426 mmol) and potassium tert-butoxide (48 mg, 0.426 mmol)

Example 69

Following general procedure I, 3-[6,7-dimethoxy-2-(2-phenyl-[1,3]dioxolan-2-yl)-benzofuran-4-yl]-2-phenylaminomethyl-acrylonitrile which was used for the next step without further purification, was obtained from the 6,7-dimethoxy-2-(2-phenyl-[1,3]dioxolan-2-yl)-benzofuran-4-carbaldehyde (2.35 g, 6.63 mmol) with 3-anilinopropionitrile (1.02 g, 6.97 mmol) and potassium tert-butoxide (0.86 g, 7.62 mmol)

MS ESI+: 483 (M+H).

Example 70

5-(2-Biphenyl-4-ylmethyl-6,7-dimethoxy-benzofuran-4-ylmethyl)-pyrimidine-2,4-diamine formic acid salt (1 mg) was obtained as a white-yellow solid after purification by prep HPLC (RP C18, 10 mM Formic acid/ACN) by reacting guanidine hydrochloride (33 mg, 0.344 mmol), potassium tert-butoxide (41 mg, 0.367 mmol) and 2-(2-biphenyl-4-ylmethyl-6,7-dimethoxy-benzofuran-4-ylmethyl-3-phenylamino-acrylonitrile (57 mg, 0.115 mmol).

MS ESI+: 467 (M+H).

Example 71

Following General Procedure J. 5-[6,7-dimethoxy-2-(4-methoxy-benzyl)benzofuran-4-ylmethyl]pyrimidine-2,4-diamine (20 mg) was obtained as a yellow solid after crystallisation from ethanol by reacting guanidine hydrochloride (17 mg, 0.18 mmol), potassium tert-butoxide (20 mg, 0.18 mmol) and 2-[6,7-dimethoxy-2-(4-methoxy-benzoyl)-benzofuran-4-ylmethyl]-3-phenylamino-acrylonitrile.

MS ESI+: 421 (M+H).

Example 72

Following General Procedure J, 5-[2-(4-fluoro-benzyl)-6,7-dimethoxy-benzofuran-4-ylmethyl]-pyrimidine-2,4-diamine hydrochloride salt (60 mg) was obtained as a dark yellow solid after crystallisation of the salt in ethrer/HCl by reacting guanidine hydrochloride (344 mg, 3.60 mmol), potassium tert-butoxide (404 mg, 3.60 mmol) and 2-[2-(4-fluoro-benzyl)-6,7-dimethoxy-benzofuran-4-ylmethyl]-3-phenylamino-acrylonitrile.

MS ESI+: 409 (M+H).

Example 73

Following General Procedure J, 5-(2-dimethylaminomethyl-6,7-dimethoxy-benzofuran-4-ylmethyl)-pyrimidine-2, 4-diamine (310 mg) was obtained as a yellow solid after crystallisation from ethanol by reacting guanidine hydrochloride (366 mg, 3.83 mmol), potassium tert-butoxide (430 mg, 3.83 mmol) and 2-(2-dimethylaminomethyl-6,7-dimethoxy-benzofuran-4-ylmethyl)-3-phenylamino-acrylonitrile.

MS ESI+: 358 (M+H).

Example 74

Following General Procedure J, 5-[2-(3,4-dihydro-1H-isoquinolin-2-ylmethyl)-6,7-dimethoxy-benzofuran-4-ylmethyl]-pyrimidine-2,4-diamine (234 mg) was obtained as a yellow solid after crystallisation from ethanol by reacting guanidine hydrochloride (245 mg, 2.56 mmol), potassium tert-butoxide (288 mg, 2.56 mmol) and 2-[2-(3,4-dihydro-1H-isoquinolin-2-ylmethyl)-6,7-dimethoxy-benzofuran-4-ylmethyl]-3-phenylamino-acrylonitrile (410 mg, 0.85 mmol)

MS ESI+: 446 (M+H).

Example 75

Following General Procedure J, 5-(6,7-dimethoxy-2-morpholin-4-ylmethyl-benzofuran-4-ylmethyl)-pyrimidine-2,4-diamine (177 mg) was obtained as a yellow solid after crystallisation from ethanol by reacting guanidine hydrochloride (228 mg, 2.39 mmol), potassium tert-butoxide (268 mg, 2.39 mmol) and 2-(6,7-dimethoxy-2-morpholin-4-ylmethyl-benzofuran-4-ylmethyl)-3-phenylamino-acrylonitrile (345 mg, 0.79 mmol).

MS ESI+: 400 (M+H).

Example 76

Following General Procedure J, 5-{2-[(4-fluoro-phenylamino)-methyl]-6,7-dimethoxy-benzofuran-4-ylmethyl}-pyrimidine-2,4-diamine (4 mg) was obtained as a yellow solid after puritfication by TLC preparative (SiO$_2$, CH$_2$Cl$_2$/MeOH, 9:1)) by reacting guanidine hydrochloride (163 mg, 1.05 mmol), potassium tert-butoxide (118 mg, 1.05 mmol) and 2-{2-[(4-fluoro-phenylamino)-methyl]-6,7-dimethoxy-benzofuran-4-ylmethyl}-3-phenylamino-acrylonitrile

MS ESI+: 424 (M+H).

Example 77

Following General Procedure J, 5-[6,7-dimethoxy-2-(4-methoxy-benzyloxymethyl)-benzofuran-4-ylmethyl]-pyrimidine-2,4-diamine (32 mg) was obtained as a yellow solid after crystallisation from ethanol by reacting guanidine hydrochloride (99 mg, 0.68 mmol), potassium tert-butoxide (76 mg, 0.68 mmol) and 2-[6,7-dimethoxy-2-(4-methoxy-benzyloxymethyl)-benzofuran-4-ylmethyl]-3-phenylamino-acrylonitrile (110 mg, 0.23 mmol)

MS ESI+: 451 (M+H).

Example 78

Following General Procedure J, 5-(2-allyloxymethyl-6,7-dimethoxy-benzofuran-4-ylmethyl)-pyrimidine-2,4-diamine (299 mg) was obtained as a yellow solid after crystallisation from ethanol by reacting guanidine hydrochloride (531 mg, 3.63 mmol), potassium tert-butoxide (408 mg, 0.68 mmol) and 2-(2-allyloxymethyl-6,7-dimethoxy-benzofuran-4-ylmethyl)-3-phenylamino-acrylonitrile (490 mg, 1.21 mmol)

MS ESI+: 371 (M+H).

Example 79

Following General Procedure J, 5-(6,7-dimethoxy-2-phenyl-benzofuran-4-ylmethyl)-pyrimidine-2,4-diamine (4 mg) was obtained as a yellow solid after crystallisation from ethanol by reacting guanidine hydrochloride (122 mg, 1.28 mmol), potassium tert-butoxide (143 mg, 1.28 mmol) and 2-(6,7-dimethoxy-2-phenyl-benzofuran-4-ylmethyl)-3-phenylamino-acrylonitrile.

MS ESI+: 377 (M+H).

Example 80

Following General Procedure J, 5-[6,7-dimethoxy-2-(2-phenyl-[1,3]dioxolan-2-yl)-benzofuran-4-ylmethyl]-pyrimidine-2,4-diamine (440 mg) was obtained as a yellow solid after crystallisation from ethanol by reacting guanidine hydrochloride (890 mg, 9.3 mmol), potassium tert-butoxide (1.04 g, 9.3 mmol) and 3-[6,7-dimethoxy-2-(2-phenyl-[1,3]dioxolan-2-yl)-benzofuran-4-yl]-2-phenylaminomethyl-acrylonitrile (1.5 g crude).

MS ESI+: 449 (M+H).

Example 81

[4-(2,4-Diamino-pyrimidin-5-ylmethyl)-6,7-dimethoxy-benzofuran-2-yl]-phenyl-methanone; hydrochloride (107 mg, 25%) was obtained as a yellow solid after crystallisation from ethanol by reacting a solution of 5-[6,7-dimethoxy-2-(2-phenyl-[1,3]dioxolan-2-yl)-benzofuran-4-ylmethyl]-pyrimidine-2,4-diamine (440 mg, 0.981 mmol) in ethanol with 6 N HCl for 16 h at r.t.

MS ESI+: 405 (M+H).

Example 82

[4-(2,4-Diamino-pyrimidin-5-ylmethyl)-6,7-dimethoxy-benzofuran-2-yl]-phenyl-methanol (10 mg) was obtained by reacting [4-(2,4-Diamino-pyrimidin-5-ylmethyl)-6,7-dimethoxy-benzofuran-2-yl]-phenyl-methanone (20 mg) with NaBH$_4$ Then the reaction was quenched with 1N HCl, the impurities were extracted with ethyl acetate and the solution neutralised with Na$_2$CO$_3$ to pH=7 and saturated with NaOAc. The compound was extracted with ACN dried over MgSO$_4$ and the solvent evaporated to give the desired compound.

MS ESI+: 407 (M+H).

Example 83

Deprotection of Hydroxyl

Under argon, to a solution of 5-(2-allyloxymethyl-6,7-dimethoxy-benzofuran-4-ylmethyl)-pyrimidine-2,4-diamine (610 mg, 1.64 mmol) in ACN was added Pd(PPh$_3$)$_4$ complex (571 mg, 0.424 mmol) and ammonium formate (519 mg, 8.23 mmol). The reaction mixture was stirred at reflux for 2 h. Then the reaction was quenched with 1N HCl, the impurities were extracted with ethyl acetate and the solution neutralised with Na$_2$CO$_3$ to pH=7 and saturated with NaOAc. The compound was extracted with ACN dried over MgSO$_4$ and the solvent evaporated to give [4-(2,4- diamino-pyrimidin-5-ylmethyl)-6,7-dimethoxy-benzofuran-2-yl]-methanol (497 mg, 84%) as a yellow solid.

General Procedure M: Protection of the Keto Group

Under argon, to a solution of compounds VI (1 eq.) in dry toluene was added ethylene glycol (6.5 eq.) and p-toluene sulfonic acid (0.15 eq.). The reaction mixture was stirred at reflux for 16 h and the water produce during the reaction was distilled using a Dean-stark trap. The reaction mixture was diluted with ether and the organic layer was washed with $H_2O$, brine and dried over $MgSO_4$. Purification by FC hexane/ethyl acetate (19:1) gave the expected compound X.

Example 84

6,7-Dimethoxy-2-(2-phenyl-[1,3]dioxolan-2-yl)-benzofuran-4-carboxylic acid methyl ester (5.08 g, 62%) was obtained as an oil by reacting 2-benzoyl-6,7-dimethoxy-benzofuran-4-caboxylic acid methyl ester (7.22 g, 21.21 mmol) with ethylene glycol (7.71 ml, 138.5 mmol) and pTsOH (609 mg, 3.2 mmol)

General Procedure N: Transformation to Chloro Derivatives

Under argon, to a solution of the alcohol (1 eq.) in ether or $CHCl_3$ was added thionyl chloride (1.5–1.7 eq.) and the reaction mixture was stirred for 1h at reflux. In the case of ether as solvent the organic layer could be washed with $H_2O$, dried over $MgSO_4$ and the solvent evaporated to give the chloride derivative VIII.2. In the case of $CHCl_3$ as solvent, the solvent and the excess of thionyl chloride were distilled under reduced pressure to give the chloride derivative XIX.

Example 85

2-Chloromethyl-6,7-dimethoxy-benzofuran-4-carboxylic acid methyl ester (1.04 g, 97%) was obtained as a yellow solid by reacting 2-hydroxymethyl-6,7-dimethoxy-benzofuran-4-carboxylic acid methyl ester (1.0 g, 3.75 mmol) with thionyl chloride (0.460 ml, 6.38 mmol) and pyridine (0.04 ml, cat.).

Example 86

[4-(2,4-Diamino-pyrimidin-5-ylmethyl)-6,7-dimethoxy-benzofuran-2-yl]-methanol (200 mg, 0.60 mmol) was reacted with thionyl chloride (0.066 ml, 0.90 mmol) to give after direct evaporation of the solvent 5-(2-chloromethyl-6,7-dimethoxy-benzofuran-4-ylmethyl)-pyrimidine-2,4-diamine as a yellow oily compound which was used in the next step without further purification.

General Procedure O: Friedel Craft's Alkylation

Under argon at 50° C., to a solution of the aromatic derivatives $R^5$ (10 eq.) in $CHCl_3$ was added $ZnCl_2$ (1.2–2.4 eq.). A solution of the chloride derivative (1 eq.) in $CHCl_3$ was then slowly added within 30 min. After stirring at 50° C. for 1–2 h the reaction was quenched with $H_2O$ and the reaction mixture was partitioned between $CH_2Cl_2$ and $NaHCO_3$ sat. The organic layer was separated, dried over $MgSO_4$ and the solvent evaporated. The pure derivatives IX were obtained after purification by FC hexane/ethyl acetate (3:1). The pure derivatives I were obtained after dissolution the crude mixture in 1N HCl, extraction of the nonpolar impurities with ether, basification with $Na_2CO_3$ to pH=8 and extraction of the compound with ethyl acetate or $CHCl_3$. The organic layer was then dried over $MgSO_4$ and the solvent evaporated to give the pure compound I.

Example 87

5-[2-(3,4-Dimethoxy-benzyl)-6,7-dimethoxy-benzofuran-4-ylmethyl]-pyrimidine-2,4-diamine (45 mg) was obtained as a dark yellow solid by reacting 5-(2-chloromethyl-6,7-dimethoxy-benzofuran-4-ylmethyl)-pyrimidine-2,4-diamine (155 mg, 0.454 mmol) with veratrol (0.529 ml, 4.45 mmol) and $ZnCl_2$ (68 mg, 0.50 mmol)

MS ESI+: 451 (M+H).

Example 88

4-[4-(2,4-Diamino-pyrimidin-5-ylmethyl)-6,7-dimethoxy-benzofuran-2-ylmethyl]-phenol (3 mg) was obtained after purification of a part of the reaction mixture by TLC prep (SiO2) as a white-yellow solid by reacting 5-(2-chloromethyl-6,7-dimethoxy-benzofuran-4-ylmethyl)-pyrimidine-2,4-diamine (50 mg, 0.143 mmol) with phenol (135 mg, 1.43 mmol) and $ZnCi_2$ (23 mg, 0.172 mmol).

MS ESI+: 407 (M+H).

Example 89

5-[6,7-Dimethoxy-2-(1-methyl-1H-pyrrol-2-ylmethyl)-benzofuran-4-ylmethyl]-pyrimidine-2,4-diamine (3 mg) was as a yellow solid by reacting 5-(2-chloromethyl-6,7-dimethoxy-benzofuran-4-ylmethyl)-pyrimidine-2,4-diamine (50 mg, 0.143 mmol) with methylpyrrole (0.128 ml, 1.43 mmol) and $ZnCl_2$ (47 mg, 0.34 mmol).

MS ESI+: 394 (M+H).

General Procedure P: Coupling

Under argon, to a solution of pyrrol, indol, thiophenol or phenol $HXR^{10}$ (1.5–2 eq.) in DMF was added NaH (1.5–2 eq.) and the mixture was stirred for 1 h. 5-(2-Chloromethyl-6,7-dimethoxy-benzofuran-4-ylmethyl)-pyrimidine-2,4-diamine (1 eq.) in DMF was then slowly added. The reaction mixture was stirred for 18 h at r.t. After quenching the reaction with $H_2O$, the mixture was partitioned between $NaHCO_3$ sat. and $CHCl_3$. The aqueous layer was extracted several times with $CHCl_3$ dried over $MgSO_4$ and the solvent was evaporated. The residue was dissolved in 1N HCl, extracted with ether, basified with $Na_2CO_3$ to pH=8 an extracted with $CHCl_3$. The $CHCl_3$ layer was dried over $MgSO_4$, the solvent evaporated to give the pure compounds I. The salts were obtained after treating the free base with the corresponding acidic aqueous solution and freeze-drying.

Example 90

5-[2-(4-Fluoro-phenoxymethyl)-6,7-dimethoxy-benzofuran-4-ylmethyl]-pyrimidine-2,4-diamine; formic acid salt (48 mg, 76%) was obtained by reacting 5-(2-chloromethyl-6,7-dimethoxy-benzofuran-4-ylmethyl)-pyrimidine-2,4-diamine (52 mg, 0.151 mmol), NaH (9 mg, 0.226 mmol), and 4-fluororphenol (25 mg, 0.226 mmol).

MS ESI+: 471 (M+H).

Example 91

5-[6,7-Dimethoxy-2-(4-trifluoromethyl-phenoxymethyl)-benzofuran-4-ylmethyl]-pyrimidine-2,4-diamine; formic acid salt (33 mg, 47%) was obtained by reacting 5-(2-chloromethyl-6,7-dimethoxy-benzofuran-4-ylmethyl)-pyrimidine-2,4-diamine (52 mg, 0.151 mmol), NaH (9 mg, 0.226 mmol), and 4-trifluorophenol (337 mg, 0.226 mmol).

MS ESI+: 521 (M+H).

Example 92

5-[2-(4-Fluoro-phenylsulfanylmethyl)-6,7-dimethoxy-benzofuran-4-ylmethyl]-pyrimidine-2,4-diamine; formic acid salt (15 mg) was obtained by reacting 5-(2-chloromethyl-6,7-dimethoxy-benzofuran-4-ylmethyl)-pyrimidine-2,4-diamine (52 mg, 0.151 mmol), NaH (12 mg, 0.303 mmol), and 4-fluorothiophenol (0.032 ml, 0.303 mmol).

MS ESI+. 487 (M+H).

Example 93

N-{4-[4-(2,4-Diamino-pyrimidin-5-ylmethyl)-6,7-dimethoxy-benzofuran-2-ylmethylsulfanyl]-phenyl}-acetamide; formic acid salt (20 mg) was obtained by reacting 5-(2-chloromethyl-6,7-dimethoxy-benzofuran-4-ylmethyl)-pyrimidine-2,4-diamine (52 mg, 0.151 mmol), NaH (12 mg, 0.303 mmol), and 4-acetaminothiophenol (56 mg, 0.303 mmol).

MS ESI+526 (M+H).

Example 94

4-[4-(2,4-Diamino-pyrimidin-5-ylmethyl)-6,7-dimethoxy-benzofuran-2-ylmethoxy]-phenol (3 mg) was obtained after purification of a part of the reaction mixture by TLC preparative ($SiO_2$) by reacting 5-(2-chloromethyl-6,7-dimethoxy-benzofuran-4-ylmethyl)-pyrimidine-2,4-diamine (75 mg, 0.215 mmol), NaH (13 mg, 0.322 mmol), and 4-hydroxyphenol (38 mg, 0.344 mmol).

MS ESI+: 423 (M+H).

Example 95

5-[2-(4-Amino-phenoxymethyl)-6,7-dimethoxy-benzofuran-4-ylmethyl]-pyrimidine-2,4-diamine (43 mg) was obtained by reacting 5-(2-chloromethyl-6,7-dimethoxy-benzofuran-4-ylmethyl)-pyrimidine-2,4-diamine (75 mg, 0.215 mmol), NaH (13 mg, 0.322 mmol), and 4-aminophenol (50 mg, 0.344 mmol).

MS ESI+:422 (M+H).

Example 96

5-(6,7-Dimethoxy-2-pyrrol-1-ylmethyl-benzofuran-4-ylmethyl)-pyrimidine-2,4-diamine (62 mg, 74%) was obtained by reacting 5-(2-chloromethyl-6,7-dimethoxy-benzofuran-4-ylmethyl)-pyrimidine-2,4-diamine (77 mg, 0.220 mmol), NaH (13 mg, 0.322 mmol), and pyrrole (0.022 ml, 0.322 mmol).

MS ESI+: 380 (M+H).

Example 97

5-(2-Imidazol-1-ylmethyl-6,7-dimethoxy-benzofuran-4-ylmethyl)-pyrimidine-2,4-diamine (24 mg, 28%) was obtained by reacting 5-(2-chloromethyl-6,7-dimethoxy-benzofuran-4-ylmethyl)-pyrimidine-2,4-diamine (77 mg, 0.220 mmol), NaH (13 mg, 0.322 mmol), and imidazol (22 mg, 0.322 mmol).

MS ESI+: 381 (M+H).

Example 98

Following procedure C, 5-(2,4-diamino-pyrimidin-5-ylmethyl)-2,3-dimethoxy-phenol (Helv. Chim. Acta 1970, 53, 945) (200 mg, 0.687 mmol) was reacted with $K_2CO_3$ (71 mg, 0.515 mmol) and ethyl-2-chloroacetoacetate (0.096 ml, 0.687 mmol) to give after work-up using $CHCl_3$ and $NaHCO_3$ sat solution and crystallisation in ethanol, 4-(2,4-diamino-pyrimidin-5-ylmethyl)-6,7-dimethoxy-3-methyl-benzofuran-2-carboxylic acid ethyl ester as a yellow solid (150 mg, 57%)

MS ESI+: 387 (M+H).

Example 99

4-(2,4-Diamino-pyrimidin-5-ylmethyl)-6,7-dimethoxy-3-methyl-benzofuran-2-carboxylic acid was (10 mg) obtained as a yellow solid after treating 4-(2,4-diamino-pyrimidin-5-ylmethyl)-6,7-dimethoxy-3-methyl-benzofuran-2-carboxylic acid ethyl ester with a 2N NaOH solution neutralisation of the solution with HCl and freeze-drying.

MS ESI+: 359 (M+H).

Example 100

Following General Procedure G, 4-(2,4-diamino-pyrimidin-5-ylmethyl)-6,7-dimethoxy-benzofuran-2-carbaldehyde (10 mg) was obtained by reacting [4-(2,4-diamino-pyrimidin-5-ylmethyl)-6,7-dimethoxy-benzofuran-2-yl]-methanol (15 mg, 0.04 mmol) and $MnO_2$ (4 mg, 0.4 mmol)

MS ESI+:329 (M+H).

Example 101

Biological Results

Antimicrobial susceptibility testing was performed in accordance with the National Committee for Clinical Laboratory Standards (NCCLS) procedure [M7-A5, 2001]. M7-A5 (2001): Methods for Dilution Antimicrobial Susceptibility Tests for Bacteria That Grow Aerobically; Approved Standard—Fifth Edition American National Standard

| | In vitro Antibacterial Activity of Compounds (Minimum Inhibitory Concentration (MIC) in micrograms/ml) | | | |
|---|---|---|---|---|
| | End Product of Example | | | |
| Microorganism | 20 | 21 | 72 | Trimethoprim |
| Escherichia coil ATCC 25922 | 4.0 | 2.0 | 2.0 | 0.25 |
| Staphylococcus aureus ATCC 25923 | 0.062 | 0.062 | 0.25 | 2 |
| Streptococcus pneumoniae ATCC 49619 | 0.125 | 0.50 | 0.5 | 2 |
| Staphylococcus epidermidis ATCC 12228 | 0.062 | 0.062 | 0.015 | 0.062 |
| Enterococcus faecalis ATCC 29212 | 0.500 | 0.125 | 1.0 | 0.5 |
| Bacillus subtilis ATCC 6051 | 0.062 | 0.062 | 0.25 | 0.5 |

What is claimed is:

1. A compound of formula

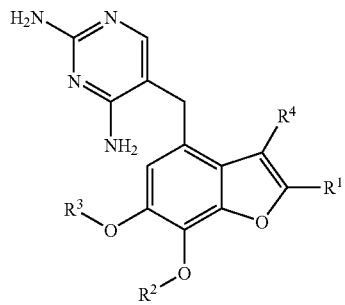

wherein $R^1$ represents cycloalkylmethyl with 3 to 6 carbon atoms; aryl; arylmethyl or heteroarymethyl, the aryl and heteroaryl group may be mono-, di- or tri-substituted with halogen, amino, hydroxy, nitro, trifluoromethyl, lower alkyloxy, lower alkylcarbonylamino, arylcarbonylamino, whereby these substituents may be the same or different; straight or branched chain lower alkylcarbonyl with up to 6 carbon atoms; cycloalkylcarbonyl with 3 to 6 carbon atoms; cycloalkylhydroxymethyl with 3 to 6 carbon atoms; arylcarbonyl, the aryl group may be mono-, di or tri-substituted with halogen, amino, lower alkyloxy, lower alkylcarbonylamino, arylcarbonylamino, whereby these substituents may be the same or different; arylhydroxymethyl, the aryl group may be mono-, di- or tri-substituted with halogen, amino, lower alkyloxy, lower alkylcarbonylamino, arylcarbonylamino, whereby these substituents may be the same or different; straight or branched chain lower alkenyl with 2 to 6 carbon atoms; hydroxy-lower alkyl with 1 to 6 carbon atoms; fluoro-lower alkyl with 1 to 6 carbon atoms; aryloxy-lower alkyl whereby the aryl group may be mono-, di- or tri-substituted with halogen, amino, lower alkyloxy, lower alkylcarbonylamino, arylcarbonylamino, whereby these substituents may be the same or different; arylthio-lower alkyl whereby the aryl group may be mono-, di- or tri-substituted with halogen, amino, lower alkyloxy, lower alkylcarbonylamino, arylcarbonylamino, whereby these substituents may be the same or different; arylamino-lower alkyl whereby the aryl group may be mono-, di- or tri-substituted with halogen, amino, lower alkyloxy, lower alkylcarbonylamino, arylcarbonylamino, whereby these substituents may be the same or different; lower alkenyloxy lower alkyl whereby the lower alkenyl group may contain 2 to 4 carbon atoms and the lower alkyl group may contain 1 or 2 carbon atoms; benzyloxy lower alkyl whereby the benzyl group may be mono-, di- or tri-substituted with halogen, amino, lower alkyloxy, lower alkylcarbonylamino, arylcarbonylamino, whereby these substituents may be the same or different; lower alkylamino lower alkyl whereby the lower alkyl groups may contain 1 to 3 carbon atoms; heterocyclylmethyl containing one to three hetero atoms which can be the same or different and which may be substituted with lower alkyl, halogen, amino, lower alkyloxy, hydroxy, lower alkylcarbonylamino, arylcarbonylamino and benzofused derivatives thereof, and wherein $R^2$ and $R^3$ independently represent hydrogen; lower alkyl with 1 to 3 carbon atoms; or together a lower alkylene group with 1 to 3 carbon atoms bridging the oxygen atoms and forming a five, six or seven membered ring; $R^4$ represents hydrogen; straight or branched chain lower alkyl with 1 to 4 carbon atoms; a pharmaceutically acceptable salt thereof; or N-oxide thereof.

2. The compound of formula

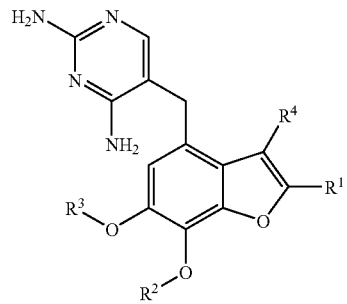

wherein $R^1$ is cycloalkylmethyl with 3 to 6 carbon atoms; aryl; arylmethyl or heteroarymethyl, the aryl and heteroaryl group may be mono- or di substituted with halogen, amino, hydroxy, nitro, trifluoromethyl, lower alkyloxy, lower alkylcarbonylamino, arylcarbonylamino, whereby these substituents may be the same or different, and $R^2$ and $R^3$ are methyl or together are a methylene group bridging the oxygen atoms to which they are attached and $R^4$ is hydrogen or methyl.

3. The compound of formula

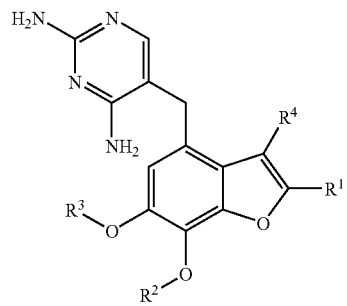

wherein $R^1$ is 4-methoxy-benzyl, phenyl, benzyl, cyclopropylmethyl, 4-fluoro-benzyl, 3,4-dihydro-1H-isoquinolin-2-ylmethyl, 4-methoxy-benzyloxymethyl, 4-acetylaminophenyl-sulfanyl-methyl, 4-trifluoromethyl-phenoxymethyl, 4-amino-phenoxymethyl, allyloxymethyl, phenyl-[1,3]dioxolan-2-yl, pyrrol-1-ylmethyl, 3,4-dimethoxy-benzyl, 4-hydroxyphenyloxylnethyl, phenylcarbonylmethyl, 4-fluoro-phenoxymethyl, 2,2-dimethyl-propyl, 4-fluoro-phenylsulfanylmethyl, hydroxymethyl, formyl, 4-fluoro-phenylamino-methyl, imidazol-1-ylmethyl, dimethylaminomethyl, morpholin-4-ylmethyl, biphenyl-4-ylmethyl, ethoxycarbonyl, carboxy, 4-hydroxybenzyl, furan-2-ylmethyl, thiophen-2-ylmethyl, thiophen-3-ylmethyl, 1-methyl-pyrrol-2-ylmethyl, pyridin-2-ylmethyl, pyridin-3-ylmethyl, pyridin-4-ylmethyl, 4-acetylaminobenzyl, 4-amino-benzyl, 4-nitrobenzyl, 4-acetylamino-3-methoxy-benzyl, 4-amino-3-methoxy-benzyl, 3-acetylamino-4-methoxy-benzyl, 3-amino-4-methoxy-benzyl, allyl, isopropenyl or halogenmethyl, and $R^2$ and $R^3$ are methyl or together are a methylen group bridging the oxygen atoms to which they are attached and R⁴ is hydrogen or methyl.

4. The compound of formula

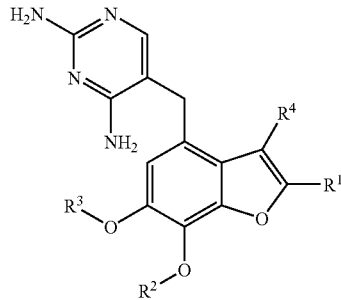

wherein R¹ is 4-methoxy-benzyl, phenyl, benzyl, cyclopropylmethyl, 4-fluoro-benzyl, 3,4-dihydro-1 H-isoquinolin-2-ylmethyl, 4-methoxy-benzyloxymethyl, 4-acetylaminophenyl-sulfanyl-methyl, 4-trifluoromethyl-phenoxymethyl, 4-amino-phenoxymethyl, allyloxymethyl, 3,4-dimethoxy-benzyl, 4-hydroxybenzyl, pyridin-2-ylmethyl, pyridin-3 -ylmethyl, pyridin-4-ylmethyl, 4-acetylaminobenzyl, 4-amino-benzyl, 4-acetylamino-3 -methoxy-benzyl, 4-amino-3-methoxy-benzyl, 3-acetylamino-4-methoxy-benzyl, 3-amino-4-methoxy-benzyl or aryl methyl and R² and R³ are both methyl and R⁴ is hydrogen.

5. The compound of formula

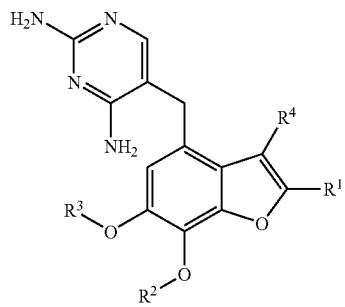

wherein R¹ is 4-methoxy-benzyl, benzyl, cyclopropylmethyl, 4-fluoro-benzyl, 3,4-dihydro-1 H-isoquinolin-2-ylmethyl, 4-amino-phenoxymethyl, 4-hydroxybenzyl, pyridin-2-ylmethyl, pyridin-3-ylmethyl, pyridin-4-ylmethyl, 4-acetylaminobenzyl, 4-amino-benzyl, 4-acetylamino-3-methoxy-benzyl, 4-amino-3-methoxy-benzyl, 3-acetylamino-4-methoxy-benzyl, 3-amino-4-methoxy-benzyl and R² and R³ are both methyl and R⁴ is hydrogen.

6. The compound according to claim 1 selected from the group consisting of

5-[6,7-Dimethoxy-2-(4-methoxy-benzyl)benzofuran-4-ylmethyl]pyrimidine-2,4-diamine, 5-(6,7-Dimethoxy-2-phenyl-benzofuran-4-ylmethyl)-pyrimidine-2,4-diamine, 5-(2-Benzyl-6,7-dimethoxy-benzofuran-4-ylmethyl)-pyrimidine-2,4-diamine, 5-(2-Cyclopropylmethyl-6,7-dimethoxy-benzofuran-4-ylmethyl)-pyrimidine-2,4-diamine, 5-[2-(4-Fluoro-benzyl)-6,7-dimethoxy-benzofuran-4-ylmethyl]-pyrimidine-2,4-diamine, 5-[2-(3,4-Dihydro-1H-isoquinolin-2-ylmethyl)-6,7-dimethoxy-benzofuran-4-ylmethyl]-pyrimidine-2,4-diamine, 5-[6,7-Dimethoxy-2-(4-methoxy-benzyloxymethyl)-benzofuran-4-ylmethyl]-pyrimidine-2,4-diamine, N-{4-[4-(2,4-Diamino-pyrimidin-5-ylmethyl)-6,7-dimethoxy-benzofuran-2-ylmethylsulfanyl]-phenyl}-acetamide, 5-[6,7-Dimethoxy-2-(4-trifluoromethyl-phenoxymethyl)-benzofuran-4-ylmethyl]-pyrimidine-2,4-diamine, 5-[2-(4-Amino-phenoxymethyl)-6,7-dimethoxy-benzofuran-4-ylmethyl]-pyrimidine-2,4-diamine, 5-(2-Allyloxymethyl-6,7-dimethoxy-benzofuran-4-ylmethyl)-pyrimidine-2,4-diamine, 5-[6,7-Dimethoxy-2-(2-phenyl-[1,3]dioxolan-2-yl)-benzofuran-4-ylmethyl]-pyrimidine-2,4-diamine, 5-(6,7-Dimethoxy-2-pyrrol-1-ylmethyl-benzofuran-4-ylmethyl)-pyrimidine-2,4-diamine, 5-[2-(3,4-Dimethoxy-benzyl)-6,7-dimethoxy-benzofuran-4-ylmethyl]-pyrimidine-2,4-diamine, 4-[4-(2,4-Diamino-pyrimidin-5-ylmethyl)-6,7-dimethoxy-benzofuran-2-ylmethoxy]-phenol, [4-(2,4-Diamino-pyrimidin-5-ylmethyl)-6,7-dimethoxy-benzofuran-2-yl]-phenyl-methanone, 5-[2-(4-Fluoro-phenoxymethyl)-6,7-dimethoxy-benzofuran-4-ylmethyl]-pyrimidine-2,4-diamine, 5-[2-(2,2-Dimethyl-propyl)-6,7-dimethoxy-benzofuran-4-ylmethyl]pyrimidine-2,4-diamine, 5-[2-(4-Fluoro-phenylsulfanylmethyl)-6,7-dimethoxy-benzofuran-4-ylmethyl]-pyrimidine-2,4-diamine,

[4-(2,4-Diamino-pyrimidin-5-ylmethyl)-6,7-dimethoxy-benzofuran-2-yl]-methanol, 4-(2,4-Diamino-pyrimidin-5-ylmethyl)-6,7-dimethoxy-benzofuran-2-carbaldehyde 5-{2-[(4-Fluoro-phenylamino)-methyl]-6,7-dimethoxy-benzofuran-4-ylmethyl}-pyrimidine-2,4-diamine, 5-(2-Imidazol-1-ylmethyl-6,7-dimethoxy-benzofuran-4-ylmethyl)-pyrimidine-2,4-diamine, 5-(2-Dimethylaminomethyl-6,7-dimethoxy-benzofuran-4-ylmethyl)-pyrimidine-2,4-diamine, 5-(6,7-Dimethoxy-2-morpholin-4-ylmethyl-benzofuran-4-ylmethyl)-pyrimidine-2,4-diamine, 5-(2-Biphenyl-4-ylmethyl-6,7-dimethoxy-benzofuran-4-ylmethyl)-pyrimidine-2,4-diamine, 4-(2,4-Diamino-pyrimidin-5-ylmethyl)-6,7-dimethoxy-3-methyl-benzofuran-2-carboxylic acid, 4-(2,4-Diamino-pyrimidin-5-ylmethyl)-6,7-dimethoxy-3-methyl-benzofuran-2-carboxylic acid ethyl ester, 5-[6,7-Dimethoxy-2-((4-chlorobenzyl)-benzofuran-4-ylmethyl]pyrimidine-2,4-diamine, 5-[6,7-Dimethoxy-2-(1-naphthylmethyl)-benzofuran-4-ylmethyl]pyrimidine-2,4-diamine, 5-[6,7-Dimethoxy-2-(2-propenyl)benzofuran-4-ylmethyl]pyrimidine-2,4-diamine, 5-(6,7-Dimethoxy-2-trifluoromethylbenzofuran-4-ylmethyl)pyrimidine-2,4-diamine, 5-[6,7-Dimethoxy-2-(2,2-dimethylpropan1-one)benzofuran-4-ylmethyl]pyrimidine-2,4-diamine, 5-[6,7-Dimethoxy-2-(cyclopropylcarbonyl)benzofuran-4-ylmethyl]pyrimidine-2,4-diamine, 5-[6,7-Dimethoxy-2-(4-methoxyphenyl-methanone)benzofuran-4-ylmethyl]pyrimidine-2,4-diamine, 5-[6,7-Dimethoxy-2-(4-chlorophenyl-methanoneI)benzofuran-4-ylmethyl]pyrimidine-2,4-diamine, 5-[6,7-Dimethoxy-2-(4-fluorophenyl-methanone)benzofuran-4-ylmethyl]pyrimidine-2,4-diamine, 5-[6,7-Dimethoxy-2-(1-naphthylmethanone)-benzofuran-4-ylmethyl]pyrimidine-2,4-diamine, 5-[6,7-Dimethoxy-2-(2,2-dimethyl-1-hydroxypropyl)-benzofuran-4-ylmethyl]-pyrimidine-2,4-diamine,
5-[6,7-Dimethoxy-2-(cyclopropylmethanol)-benzofuran-4-ylmethyl]pyrimidine-2,4-diamine,
5-[6,7-Dimethoxy-2-(phenylmethanol)benzofuran-4-ylmethyl]pyrimidine-2,4-diamine,
5-[6,7-Dimethoxy-2-((4-methoxyphenylmethanol)-benzofuran-4-ylmethyl]pyrimidine-2,4-diamine,
5-[6,7-Dimethoxy-2-((4-chlorophenyl)methanol)-benzofuran-4-ylmethyl]pyrimidine-2,4-diamine,
5-[6,7-Dimethoxy-2-((4-fluorophenylmethanol)-benzofuran-4-ylmethyl]pyrimidine-2,4-diamine,
5-[6,7-Dimethoxy-2-(1-naphthylmethanol)-benzofuran-4-ylmethyl]pyrimidine-2,4-diamine,
5-[2-(3,4-Dihydro-2H-quinolin-1-ylmethyl)-6,7-dimethoxy-benzofuran-4-ylmethyl]-pyrimidine-2,4-diamine,
5-[6,7-Dimethoxy-2-(tetrazol-5-ylmethyl)benzofuran-4-ylmethyl]pyrimidine-2,4-diamine,
5-[6,7-Dimethoxy-2-(indol-1-ylmethyl)benzofuran-4-ylmethyl]pyrimidine-2,4-diamine,
5-[6,7-Dimethoxy-2-(imidazol-1-ylcarbonyl)benzofuran-4-ylmethyl]pyrimidine-2,4-diamine,
5-(2-Furan-2-ylmethyl-6,7-dimethoxy-benzofuran-4-ylmethyl)-pyrimidine-0,4-diamine,
5-(6,7-Dimethoxy-2-thiophen -2-ylmethyl-benzofuran-4-ylmethyl)-pyrimidine-2,4-diamine,
5-[6,7-Dimethoxy-2-(1-methyl-1H-pyrrol-2-ylmethyl)-benzofuran-4-ylmethyl]-pyrimidine-2,4-diamine,
5-(6,7-Dimethoxy-2-pyridin-2-ylmethyl-benzofuran-4-ylmethyl)-pyrimidine-2,4-diamine,
5-(6,7-Dimethoxy-2-pyridin-3-ylmethyl-benzofuran-4-ylmethyl)-pyrimidine-2,4-diamine,
5-(6,7-Dimethoxy-2-pyridin-4-ylmethyl-benzofuran-4-ylmethyl)-pyrimidine-2,4-diamine,
4-[4-(2,4-Diamino-pyrimidin-5-ylmethyl)-6,7-dimethoxy-benzofuran-2-ylmethyl]-phenol,
N-{4-[4-(2,4-Diamino-pyrimidin-5-ylmethyl)-6,7-dimethoxy-benzofuran-2-ylmethyl]-phenyl}-acetamide,
5-[2-(4-Amino-benzyl)-6,7-dimethoxy-benzofuran-4-ylmethyl]-pyrimidine-2,4-diamine,
5-[6,7-Dimethoxy-2-(4-nitro-benzyl)-benzofuran-4-ylmethyl]-pyrimidine-2,4-diamine,
N-{4-[4-(2,4-Diamino-pyrimidin-5-ylmethyl)-6,7-dimethoxy-benzofuran-2-ylmethyl]-2-methoxy-phenyl}-acetamide,
5-[2-(4-Amino-3-methoxy-benzyl)-6,7-dimethoxy-benzofuran-4-ylmethyl]-pyrimidine-2,4-diamine,
N-{5-[4-(2,4-Diamino-pyrimidin-5-ylmethyl)-6,7-dimethoxy-benzofuran-2-ylmethyl]-2-methoxy-phenyl}-acetamide,
5-[2-(3-Amino-4-methoxy-benzyl)-6,7-dimethoxy-benzofuran-4-ylmethyl]-pyrimidine-2,4-diamine, and
5-(6,7-Dimethoxy-2-thiophen-3-ylmethyl-benzofuran-4-ylmethyl)-pyrimidine-2,4-diamine, or a pharmaceutically acceptable salt or N-oxide thereof.

7. A pharmaceutical composition containing a compound of claim 1, 2, 3, 4, or 5 and at least one pharmaceutically acceptable carrier material or adjuvant.

8. A pharmaceutical composition for the treatment of an infection caused by *Escherichia coli, Staphylococcus aureus, Streptococcus pneumoniae, Staphylococcus epidermidis, Enterococcus faecalis* or *Bacillus subtilis*, containing a compound of claim 1, 2, 3, 4, or 5 and at least one pharmaceutically acceptable carrier material or adjuvant.

9. A pharmaceutical composition containing a compound of claim 6 and a pharmaceutically acceptable carrier material or adjuvant.

10. A pharmaceutical composition for the treatment of an infection caused by *Escherichia coli, Staphylococcus aureus, Streptococcus pneumoniae, Staphylococcus epidermidis, Enterococcus faecalis* or *Bacillus subtilis*, containing a compound of claim 6 and a pharmaceutically acceptable carrier material or adjuvant.

11. A process for the manufacture of a pharmaceutical composition, which process comprises mixing at least one compound of claim 1, 2, 3, 4, or 5 with at least one pharmaceutically acceptable excipient.

12. A process for the manufacture of a pharmaceutical composition for the treatment of an infection caused by *Escherichia coli, Staphylococcus aureus, Streptococcus pneumoniae, Staphylococcus epidermidis, Enterococcus faecalis* or *Bacillus subtilis*, which process comprises mixing at least one compound of claim 1, 2, 3, 4, or 5 with at least one pharmaceutically acceptable excipient.

13. A process for the manufacture of a pharmaceutical composition comprising mixing a compound of claim 6 with a pharmaceutically acceptable excipient.

14. A process for the manufacture of a pharmaceutical composition for the treatment of an infection caused by *Escherichia coli, Staphylococcus aureus, Streptococcus pneumoniae, Staphylococcus epidermidis, Enterococcus faecalis* or *Bacillus subtilis*, comprising mixing a compound of claim 6 with a pharmaceutically acceptable excipient.

15. A method for using at least one compound of claim 1, 2, 3, 4, or 5 for the treatment of an infection caused by *Escherichia coli, Staphylococcus aureus, Streptococcus pneumoniae, Staphylococcus epidermidis, Enterococcus faecalis* or *Bacillus subtilis* which method comprises administering an effective amount of said compound to a patient in need thereof.

16. A method for using the compound of claim 6 to treat an infection caused by *Escherichia coli, Staphylococcus aureus, Streptococcus pneumoniae, Staphylococcus epidermidis, Enterococcus faecalis* or *Bacillus subtilis* which method comprises administering an effective amount of said compound to a patient in need thereof.

* * * * *